(12) United States Patent
White

(10) Patent No.: US 7,001,346 B2
(45) Date of Patent: Feb. 21, 2006

(54) APPARATUS AND METHODS FOR MAKING INTRAOPERATIVE ORTHOPEDIC MEASUREMENTS

(75) Inventor: Michael R. White, 4747 Forest Ridge Ct., Rochester, MI (US) 48306

(73) Assignee: Michael R. White, Rochester, MI (US)

( * ) Notice: Subject to any disclaimer, the term of this patent is extended or adjusted under 35 U.S.C. 154(b) by 317 days.

(21) Appl. No.: 10/294,831

(22) Filed: Nov. 14, 2002

(65) Prior Publication Data

US 2003/0105470 A1 Jun. 5, 2003

Related U.S. Application Data

(60) Provisional application No. 60/332,686, filed on Nov. 14, 2001.

(51) Int. Cl.
 *A61B 5/103* (2006.01)
 *A61B 5/117* (2006.01)
(52) U.S. Cl. .................................................. 600/587
(58) Field of Classification Search ................ 600/587, 600/595, 426, 591, 429; 606/61, 62, 69, 606/86, 72, 73, 1, 83, 232, 130, 87, 96; 33/700; 73/1.79; 623/16.11, 13.14; 128/898; 433/7, 433/18, 173, 24; 411/28, 79
See application file for complete search history.

(56) References Cited

U.S. PATENT DOCUMENTS

| | | | |
|---|---|---|---|
| 5,249,581 A | 10/1993 | Horbal et al. ............... 128/664 |
| 5,279,309 A * | 1/1994 | Taylor et al. ............... 600/595 |
| 5,603,717 A | 2/1997 | Benson ........................ 606/102 |
| 5,611,353 A | 3/1997 | Dance et al. ............... 128/782 |
| 6,002,859 A | 12/1999 | DiGioia, III et al. ... 395/500.32 |
| 6,074,394 A * | 6/2000 | Krause ......................... 606/86 |
| 6,241,735 B1 | 6/2001 | Marmulla .................... 606/102 |
| 6,261,247 B1 * | 7/2001 | Ishikawa et al. ............ 600/587 |
| 6,430,434 B1 * | 8/2002 | Mittelstadt .................. 600/426 |
| 6,503,249 B1 * | 1/2003 | Krause ......................... 606/62 |

FOREIGN PATENT DOCUMENTS

| | | |
|---|---|---|
| DE | 201 15 254 | 12/2001 |
| WO | WO 99/23956 | 5/1999 |
| WO | WO 00/48507 | 8/2000 |
| WO | WO 01/30257 | 5/2001 |

* cited by examiner

*Primary Examiner*—Max F. Hindenburg
*Assistant Examiner*—Brian Szmal
(74) *Attorney, Agent, or Firm*—Fish & Neave IP Group Ropes & Gray LLP; Jeffrey C. Aldridge

(57) ABSTRACT

Apparatus and methods for making intraoperative orthopedic measurements are provided. Using telemetry devices attached to a patient, relative measurements of the positions and orientations of the patient's bones may be determined. Using the relative measurements of the positions and orientations of the patient's bones, a differential measurement may be determined in connection with the orthopedic medical procedure.

64 Claims, 18 Drawing Sheets

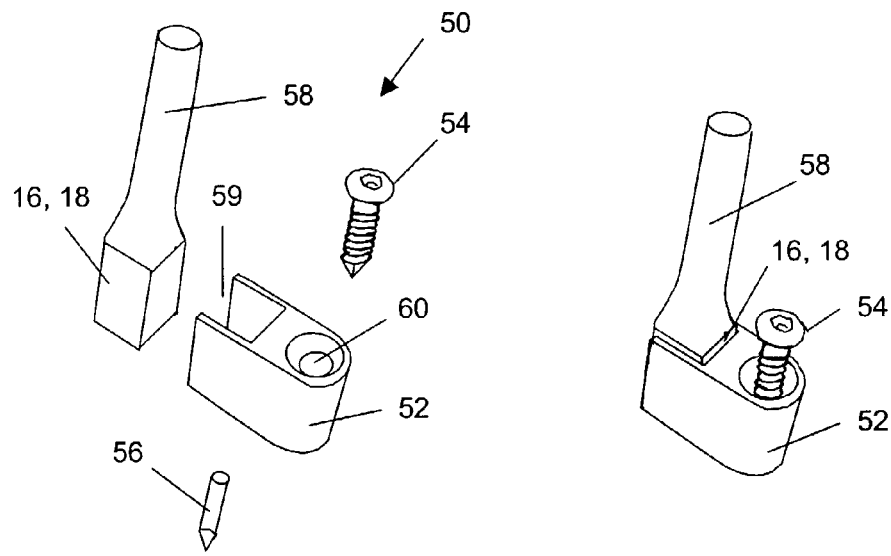
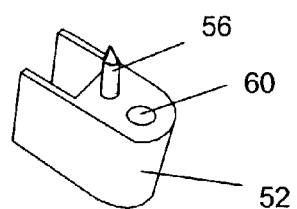
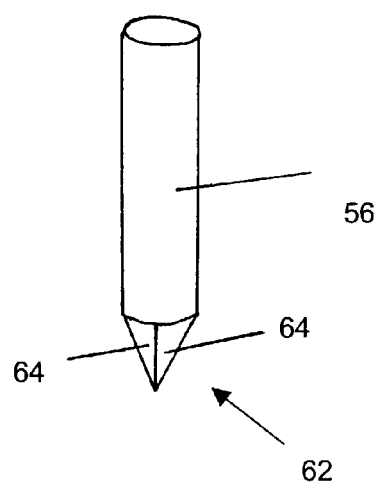
FIG. 4  FIG. 5
FIG. 6  FIG. 7

FIG. 29

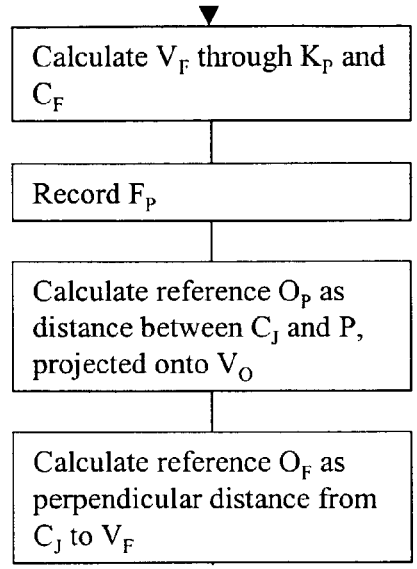

From FIG. 27

- Calculate $V_F$ through $K_P$ and $C_F$
- Record $F_P$
- Calculate reference $O_P$ as distance between $C_J$ and P, projected onto $V_O$
- Calculate reference $O_F$ as perpendicular distance from $C_J$ to $V_F$ ▶ To FIG. 27

FIG. 30

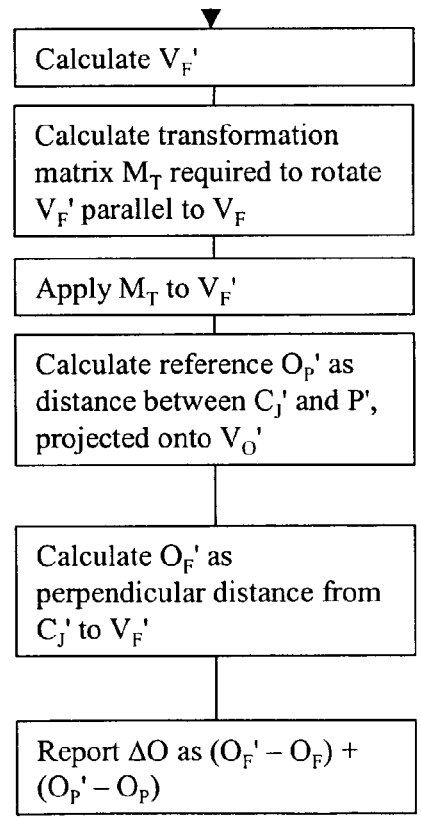

From FIG. 28

- Calculate $V_F'$
- Calculate transformation matrix $M_T$ required to rotate $V_F'$ parallel to $V_F$
- Apply $M_T$ to $V_F'$
- Calculate reference $O_P'$ as distance between $C_J'$ and P', projected onto $V_O'$
- Calculate $O_F'$ as perpendicular distance from $C_J'$ to $V_F'$
- Report $\Delta O$ as $(O_F' - O_F) + (O_P' - O_P)$ ▶ To FIG. 28

APPARATUS AND METHODS FOR MAKING INTRAOPERATIVE ORTHOPEDIC MEASUREMENTS

This application claims the benefit of U.S. provisional patent application No. 60/332,686, filed Nov. 14, 2001, which is hereby incorporated by reference herein in its entirety.

BACKGROUND OF THE INVENTION

This invention relates to apparatus and methods for making intraoperative orthopedic measurements. More particularly, this invention relates to apparatus and methods for making measurements during an orthopedic medical procedure that are related to, for example, the positions and orientations of a patient's bones.

There are many orthopedic medical procedures in which it is necessary for a surgeon to make relative measurements of the positions and orientations of a patient's bones. A surgeon may make such measurements, for example, to assist in placing a patient's bones in the appropriate relationship to one another at the termination of an orthopedic medical procedure. The relative measurements of the positions and orientations of a patient's bones provide the surgeon with a differential measurement, which is defined as the difference between a current relative position and orientation of the bones (i.e., the relative position and orientation of the bones at some time during an orthopedic medical procedure) and the initial relative position and orientation of the bones (i.e., the relative position and orientation of the bones prior to the orthopedic medical procedure). The surgeon can use the differential measurement to, for example, return the patient's bones to their initial relative position and orientation at the termination of the orthopedic medical procedure. In another example, the surgeon can use the differential measurement to place the patient's bones in a relationship to one another that is different than the initial relative position and orientation to correct an existing anatomical problem.

Historically, orthopedic surgeons have used various devices to determine a differential measurement. For example, surgeons have used mechanical measurement devices to determine a differential measurement. However, mechanical measurement devices can be affected by measurement ambiguity and are typically invasive, thereby causing additional trauma to a patient by securing various components of the devices to the patient. Furthermore, many of these devices require the patient either to remain in a fixed position during the procedure or to return to a particular position prior to the termination of the procedure to determine a differential measurement. However, since a patient is typically shifted from an initial position during the procedure, either holding the patient in a fixed position or returning the patient to a particular position can be difficult.

In another example, surgeons have used devices such as positional measurement devices to determine a differential measurement. Positional measurement devices provide a surgeon with greater accuracy in determining the differential measurement than the mechanical measurement devices described hereinabove. However, the existing positional measurement devices are large, thereby restricting a surgeon's motion during an orthopedic medical procedure, and costly. Illustrative positional measurement devices are described in, for example, Horbal et al. U.S. Pat. No. 5,249,581 and Marmulla U.S. Pat. No. 6,241,735.

A total hip arthroplasty ("THA"), also known as a hip joint replacement procedure, is an example of an orthopedic medical procedure that benefits from making intraoperative orthopedic measurements. Mechanical measurement devices for making orthopedic measurements in hip joint replacement procedures have the drawbacks as outlined hereinabove, such as measurement ambiguity and invasiveness. An example of a mechanical measurement device for use in a hip joint replacement procedure is described in Benson U.S. Pat. No. 5,603,717.

The existing positional measurement devices for making orthopedic measurements in hip joint replacement procedures have the drawbacks as outlined hereinabove, such as size and cost. In addition, the existing positional measurement devices used in hip joint replacement procedures can require substantial changes to the standard procedure to, for example, accommodate optical sensors used to make the intraoperative orthopedic measurements in some of the positional measurement device systems. In some of the existing positional measurement device systems involving optical sensors, light-emitting diodes ("LEDs") are used as bone markers. (An example of a positional measurement device system involving LEDs is described in DiGioia, III et al. U.S. Pat. No. 6,002,859.) The LEDs require an unobstructed line of sight to the optical sensor device. This forces the surgeon to perform the hip joint replacement procedure from what is often a sub-optimal location. In addition, the LED bone markers need to be attached in multiple positions on the patient, which can be difficult since the bone markers are relatively large and the exposed bone area is relatively small.

Accordingly, it would be desirable to provide improved apparatus and methods for making intraoperative orthopedic measurements that are related to, for example, the positions and orientations of a patient's bones.

SUMMARY OF THE INVENTION

In accordance with this invention, apparatus and methods for making intraoperative orthopedic measurements that are related to, for example, the positions and orientations of a patient's bones, are provided.

In certain of its aspects this invention may include methods for making orthopedic measurements during an orthopedic medical procedure. Telemetry devices are attached to a patient, and each telemetry device is connected to a processing device via a communication link. An indication may be received that the telemetry devices are in a first position. The first position of the telemetry devices may be recorded. An indication may be received that the telemetry devices are in a second position. The second position of the telemetry devices may be recorded. Based on the first and second positions, a differential measurement may be determined in connection with the orthopedic medical procedure.

In another of its aspects this invention may include apparatus having a processing device for making orthopedic measurements during an orthopedic medical procedure. Telemetry devices are attached to a patient, and each telemetry device is connected to the processing device. The processing device may comprise a storage device and a processor that is connected to the storage device. The storage device may store a processing device program for controlling the processor. The processor is operative with the processing device program to receive an indication that the telemetry devices are in a first position and to record the first position. The processor is operative with the processing device program to receive an indication that the telemetry devices are in a second position and to record the second position. The processor is operative with the processing device program to determine a differential measurement in connection with the orthopedic medical procedure that is based on the first and second positions.

In still other aspects this invention may include apparatus for attachment of a telemetry device to a bone of a patient in an orthopedic medical procedure. The apparatus may include a U-shaped piece having a front face and a back face, a bone screw, and an anti-rotation pin. The U-shaped piece may have a hole extending therethrough from the front face to the back face for receiving the bone screw. The anti-rotation pin extends from the back face of the U-shaped piece.

In yet other aspects this invention may include apparatus for attachment of a telemetry device to a bone of a patient. The apparatus may include a U-shaped channel for receiving the telemetry device that has two side portions and a base portion. The apparatus may also include a plurality of pins that have sharpened end portions for insertion into the bone. The U-shaped channel has a plurality of holes to receive the plurality of pins.

In certain of its aspects this invention may include methods for making orthopedic measurements for use in an orthopedic procedure on a patient comprising attaching a plurality of telemetry devices to the patient and monitoring locations of the telemetry devices multiple times relative to performance of the procedure. For example, the monitoring may be done before the procedure begins (i.e., before any actual orthopedic work or treatment is performed) and again when the actual orthopedic work is in progress. The method may include computing an orthopedic characteristic of the patient from results of the monitoring. An orthopedic procedure with which this invention may be used may involve temporary orthopedic separation of two parts of the patient's body, and a respective one of the telemetry devices may be attached to each of those parts. An orthopedic procedure with which this invention may be used may involve replacement of a joint in the patient with an artificial joint, and the method of this invention may then be used to provide information to facilitate installing the artificial joint to substantially replicate performance of the replaced joint. For example, the method of this invention may include determining a center of flexure of the joint to be replaced so that the center of flexure of the artificial joint can be similarly located. Other joint characteristics may be similarly determined in order to facilitate subsequent replication by the artificial joint. As another example of possible use of this invention, the orthopedic procedure may involve orthopedic treatment of the relative locations of two orthopedic structures (as in the need to increase or decrease the length of a bone), in which case this invention may include use of the monitored telemetry devices to determine the relative locations of the two orthopedic structures.

This invention may include recording at least some of the results of the monitoring of the locations of the telemetry devices. For example, the results of such monitoring prior to the actual orthopedic work or treatment may be recorded. This invention may include comparing such recorded results to the results of subsequent monitoring during the actual orthopedic work or treatment. The monitoring of this invention may include determining in three dimensions the location of each of the telemetry devices.

In another of its aspects this invention may include attaching a telemetry device to an orthopedic structure of the patient.

In still other aspects this invention may include apparatus for making measurements for use in an orthopedic procedure on a patient comprising a plurality of telemetry devices attachable to the patient and componentry for monitoring locations of the telemetry devices. The componentry may include a memory for recording at least two monitored locations for each of the telemetry devices. The componentry may further include processing circuitry for computing an orthopedic parameter of the patient based at least in part on at least two monitored locations of the telemetry devices. The telemetry devices may include sensor components for sensing location of the telemetry device in a radiant field. The telemetry devices may further include components for outputting an indication of the sensed location in the field. The telemetry devices may further include a radiant field source. The apparatus preferably does not depend on unobstructed lines of sight to, from, or between the telemetry devices.

In yet other aspects of this invention a telemetry device may include structure for securing the device to an orthopedic structure of the patient. Alternatively, the apparatus of this invention may include structure for attaching a telemetry device to an orthopedic structure of the patient. The telemetry device may be mountable on the structure for attaching after the structure for attaching has been attached to the orthopedic structure. The structure for attaching may be configured to prevent rotation relative to the orthopedic structure. The structure for attaching may include a bone screw and/or a pin for penetrating bone. The structure for attaching may include a removable structure for facilitating attachment of the structure for attaching to the orthopedic structure. The structure for attaching may be configured to receive the telemetry device after removal of the removable structure.

Further features of the invention, its nature and various advantages will be more apparent from the accompanying drawings and the following detailed description.

BRIEF DESCRIPTION OF THE DRAWINGS

FIGS. 4–7 show illustrative attachment apparatus suitable for attachment of a telemetry device to a patient in accordance with this invention.

FIGS. 27–34 are flow charts of illustrative steps involved in the performance of the various algorithms shown in FIGS. 18–26 by the measurement application in connection with a hip joint replacement procedure in accordance with this invention.

DETAILED DESCRIPTION OF THE PREFERRED EMBODIMENTS

Figure 1:
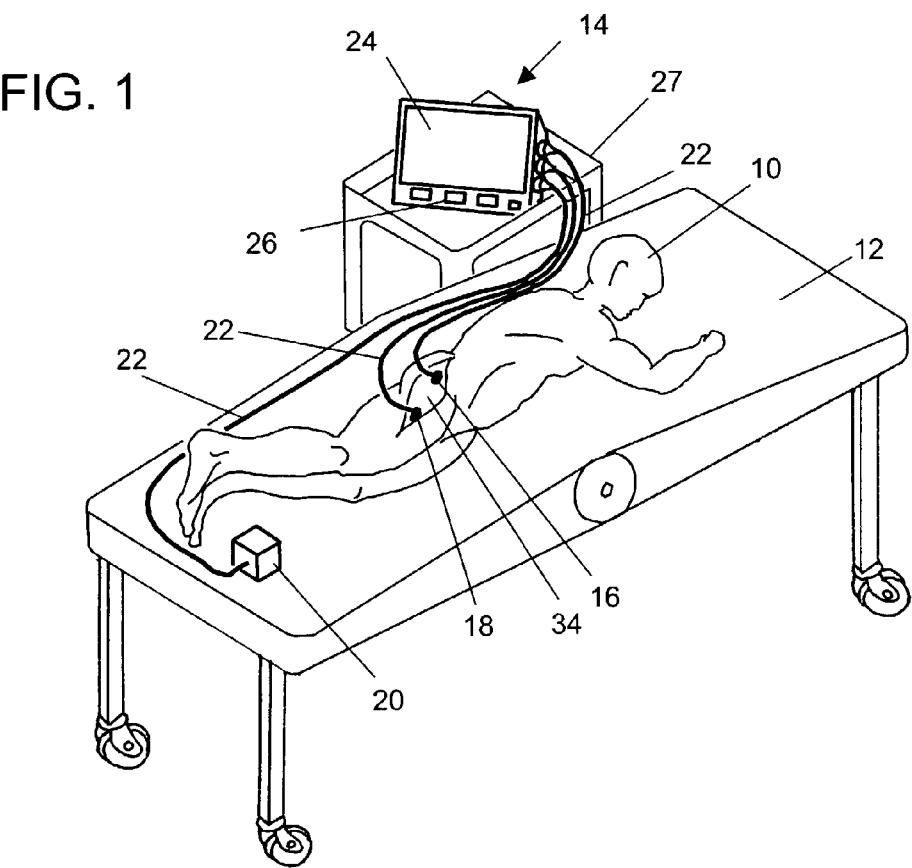
FIG. 1 is a schematic diagram of an illustrative system for making intraoperative orthopedic measurements in accordance with this invention.

FIG. 1 is a simplified schematic diagram of an illustrative system for making intraoperative orthopedic measurements in accordance with this invention. As shown in the FIG., patient 10 is prepared for a total hip arthroplasty ("THA"), also known as a hip joint replacement procedure. However, the example of this FIG. is merely illustrative, and patient 10 may be prepared for any suitable orthopedic medical procedure. In particular, the apparatus and methods of this invention for making intraoperative measurements are suitable in connection with any orthopedic medical procedure in which a surgeon requires assistance in placing a patient's bones in the appropriate relationship to one another at the termination of the orthopedic medical procedure. Such orthopedic medical procedures may include, for example, a partial or total joint replacement procedure (e.g., a knee joint replacement procedure), a femoral rod implant procedure (e.g., for fracture stabilization), or any other suitable orthopedic medical procedure.

The relative measurements of the positions and orientations of the patient's bones, as provided by the apparatus and methods of this invention, provide a surgeon with a differential measurement, which is defined as the difference between a current relative position and orientation of the bones (i.e., the relative position and orientation of the bones at some time during an orthopedic medical procedure) and the initial relative position and orientation of the bones (i.e., the relative position and orientation of the bones prior to the orthopedic medical procedure). The surgeon can use the differential measurement to, for example, return the patient's bones to their initial relative position and orientation at the termination of the orthopedic medical procedure. In another example, the surgeon can use the differential measurement to place the patient's bones in a relationship to one another that is different than the initial relative position and orientation to correct an existing anatomical problem.

As stated hereinabove, and as shown in the FIG., patient 10 is prepared for a hip joint replacement procedure. Patient 10 is located in an operating area for performance of the hip joint replacement procedure. For the duration of the procedure, patient 10 may rest on operating table 12.

Apparatus of this invention for making intraoperative orthopedic measurements include processing device 14, first electromagnetic receiver 16, second electromagnetic receiver 18, and magnetic field generator 20. First electromagnetic receiver 16, second electromagnetic receiver 18, and magnetic field generator 20 are attached to processing device 14 by communication links 22. As shown in the FIG., communication links 22 are wired connections between receivers 16 and 18, magnetic field generator 20, and processing device 14. However, this example is merely illustrative, and one or more of communication links 22 may be a wireless connection, thereby permitting one or more of receivers 16 and 18 and magnetic field generator 20 to be in wireless communication with processing device 14.

Figure 3:
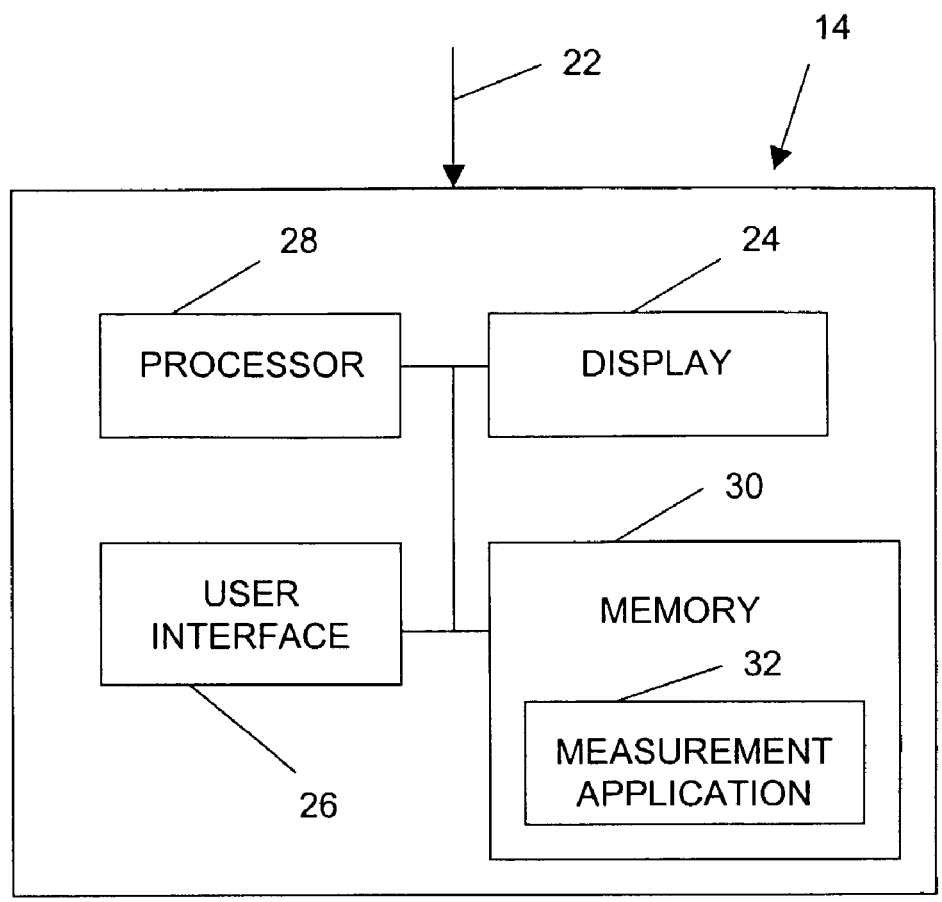
FIG. 3 is a schematic block diagram of an illustrative processing device that may be used to implement a measurement application in accordance with this invention.

As shown in the FIG., processing device 14 includes a display 24 and a user interface 26. Processing device 14 may rest on equipment cart 27 for the duration of the procedure. Processing device 14 is illustrated in more detail in FIG. 3. As shown in FIG. 3, processing device 14 may include display 24, user interface 26, processor 28, and memory 30, which may be interconnected. In a preferred embodiment, memory 30 contains a storage device for storing a processing device program for controlling processor 28. Memory 30 also preferably contains a measurement application 32 in accordance with this invention. Measurement application 32 may be used to, for example, determine a differential measurement, based on relative position and orientation information received via communication link 22.

Processor 28 uses the processing device program stored in memory 30 to present on display 24, for example, information in connection with the relative positions and orientations of the bones of patient 10 (see, for example, FIG. 2, which is described in more detail hereinbelow). User interface 26 may be used to, for example, manually initiate the determination of a differential measurement. As shown in FIG. 3, display 24 and user interface 26 are integral with, or local to, processing device 14. This example is merely illustrative. One or both of display 24 and user interface 26 may be remote to processing device 14.

Referring back to FIG. 1, first electromagnetic receiver 16 and second electromagnetic receiver 18 are attached to patient 10. In this example, receivers 16 and 18 are electromagnetic receivers and are used in conjunction with magnetic field generator 20. Magnetic field generator 20 generates a magnetic field, and receivers 16 and 18 in turn receive electromagnetic waves as generated by generator 20. Upon receipt of the electromagnetic waves, receivers 16 and 18 transmit position and orientation information via communication links 22 to processing device 14. This example, in which two electromagnetic receivers 16 and 18 are attached to patient 10 and are used in conjunction with a separate magnetic field generator 20 is merely illustrative. In an alternative embodiment, a magnetic field generator may be attached to a patient in place of one of the two electromagnetic receivers 16 and 18 and may be used in conjunction with the sole electromagnetic receiver attached to the patient. For example, the set-up may involve electromagnetic receiver 18 attached to femur 44, used in conjunction with a magnetic field generator (not shown) attached to pelvis 40. In such an embodiment, the magnetic field generator is comparable in size to the electromagnetic receiver that is attached to the patient (e.g., electromagnetic receiver 18). The position and orientation information transmitted from the electromagnetic receiver to processing device 14 is the position of the receiver relative to the magnetic field generator.

The example of FIG. 1, in which electromagnetic telemetric position monitoring technology is used, is merely illustrative, and any suitable telemetric position monitoring technology may be used. For example, wireless radio frequency ("RF") telemetry devices may be used in place of electromagnetic receivers 16 and 18 and magnetic field generator 20. In another example, transmitters may be used in place of receivers (e.g., receivers 16 and 18), in conjunction with an appropriate sensing technology.

Figure 2:
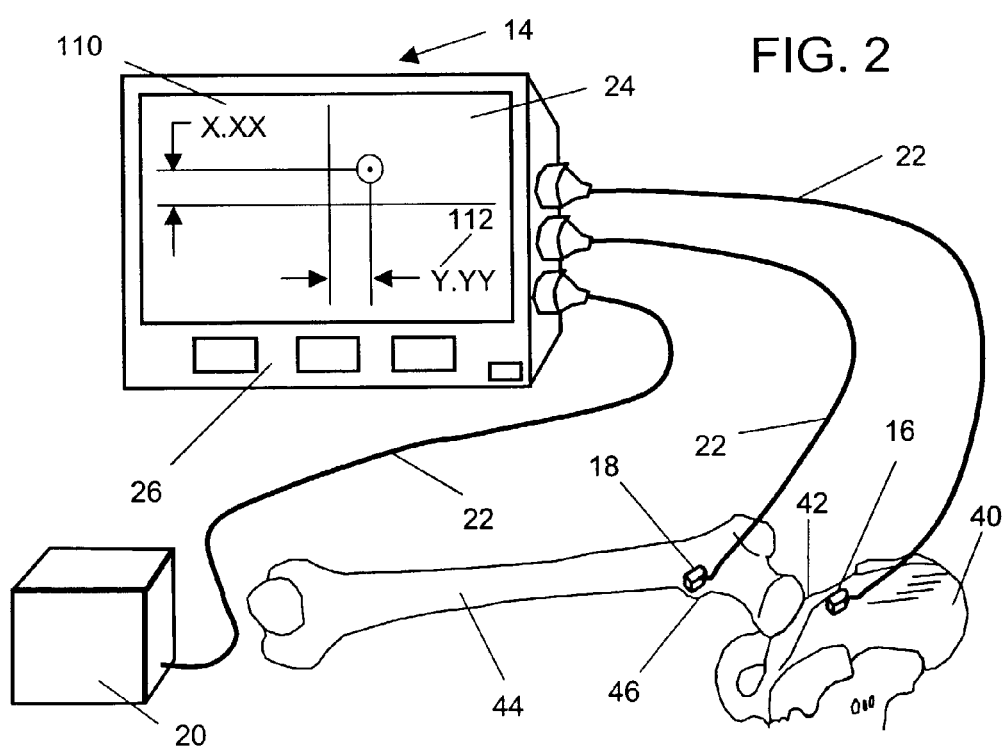
FIG. 2 is a schematic diagram of various apparatus of FIG. 1 in accordance with this invention.

FIG. 2 shows a simplified schematic diagram of some of the apparatus of FIG. 1, particularly, processing device 14, first electromagnetic receiver 16, second electromagnetic receiver 18, and magnetic field generator 20. Such apparatus (i.e., processing device 14, first electromagnetic receiver 16, second electromagnetic receiver 18, and magnetic field generator 20) are available commercially in the Flock of Birds® system, sold by Ascension Technology Corporation of Burlington, Vt. FIG. 2, for simplification, does not show the entirety of patient 10, but rather only shows the bones of patient 10 to which receivers 16 and 18 are attached (i.e., pelvis 40 and femur 44).

As in a typical hip joint replacement procedure, patient 10 is prepared by making an incision 34 (FIG. 1) in the patient, thereby exposing the hip joint. After the incision is made, first electromagnetic receiver 16 and second electromagnetic receiver 18 are attached to patient 10. (It should be noted that only second electromagnetic receiver 18 may be attached initially, to allow the surgeon to establish a reference direction using first electromagnetic receiver 16. After the reference direction has been established, first electromagnetic receiver 16 may then be attached to patient 10. This is described in more detail hereinbelow in reference to FIG. 12.) For a hip joint replacement procedure, the preferred attachment location for first electromagnetic receiver 16 is on pelvis 40 near acetabulum 42, and the preferred attachment location for second electromagnetic receiver 18 is on femur 44 near lesser trochanter 46. However, the example of FIG. 2 is merely illustrative, and the surgeon can attach receivers 16 and 18 to any suitable locations on patient 10.

Receivers 16 and 18 may be attached to pelvis 40 and femur 44, respectively, using any suitable apparatus and methods for attachment.

FIGS. 4–7 show attachment apparatus suitable for attachment of telemetry devices, such as receivers 16 and 18, to patient 10 (FIG. 1). As shown in FIG. 4, attachment assembly 50 includes receiver holder 52, bone screw 54, and anti-rotation pin 56. Also shown in FIG. 4 is one of either receiver 16 or receiver 18 (referred to herein for simplicity as "receiver 16, 18"). Attached to receiver 16, 18 is wire sleeve 58 that is used to house the end of wire 22 (FIG. 1) that attaches to the receiver.

Holder 52 may be constructed of a rigid material such as, for example, a stainless steel, titanium, a plastic (e.g., polyethylene ("PE"), polyethylene terephthalate ("PET"), polypropylene ("PP"), polystyrene ("PS"), polycarbonate ("PC")), or any other suitable material. In embodiments of this invention that use electromagnetic telemetric position monitoring technology (e.g., electromagnetic receiver 16, 18), receiver holder 52 is preferably constructed of a non-magnetic material. For attachment to patient 10 (FIG. 1), receiver 16, 18 is attached to holder 52, as shown in FIG. 5. In one example, receiver 16, 18 may be attached to holder 52 using adhesive. In another example, the housing of receiver 16, 18 (i.e., the casing around the electromagnetic receiver elements of receiver 16, 18) may be integral with holder 52. For example, both holder 52 and the housing of receiver 16, 18 may be a one-piece plastic injection molding. In yet another example, receiver 16, 18 may be attached to holder 52 using a snap-fit, in which the receiver snaps into opening 59 of the holder.

Bone screw 54 may be constructed of a metal such as a stainless steel or titanium. In embodiments of this invention that use electromagnetic telemetric position monitoring technology (e.g., electromagnetic receiver 16, 18), bone screw 54 is preferably constructed of a non-magnetic material. Bone screw 54 may be inserted into hole 60 for attachment of holder 52 to a bone of patient 10 (FIG. 1).

Bone screw 54 may be retained within hole 60 of holder 52 so that the bone screw does not separate from assembly 50 during use in an orthopedic medical procedure. In one example, hole 60 may have a diameter that is slightly smaller than the diameter of the shaft of bone screw 54, thereby creating an interference fit between the hole and the bone screw. In another example, a retaining clip may be used around the portion of the shaft of bone screw 54 that extends from holder 52. In yet another example, the diameter of bone screw 54 at the base of its shaft (i.e., the area of the shaft that is furthest from the head of the bone screw) may be slightly larger than the diameter of hole 60.

In the preferred embodiment, bone screw 54 is self-tapping. This allows the surgeon to insert bone screw 54 into a bone without first drilling a hole in the bone. In another embodiment, bone screw 54 may not be a self-tapping screw, and may instead be inserted into a pre-drilled hole in a bone. Bone screw 54 has a receptor in its head for interaction with a driving device. In the example shown, bone screw 54 has a hexagonal receptor for interaction with a driving device having a hexagonal driver portion. This example is merely illustrative, and bone screw 54 may have any suitably shaped receptor for interaction with a driver portion of a driving device.

Anti-rotation pin 56 may be constructed of a metal such as a stainless steel or titanium. In embodiments of this invention that use electromagnetic telemetric position monitoring technology (e.g., electromagnetic receiver 16, 18), anti-rotation pin 56 is preferably constructed of a non-magnetic material. Alternatively, anti-rotation pin 56 may be integral with holder 52. For example, both holder 52 and pin 56 may be a one-piece plastic injection molding.

Anti-rotation pin 56 extends from holder 52 (FIG. 6) for insertion into the bone. Anti-rotation pin 56 prevents attachment assembly 50 from rotating once the assembly is attached to a bone. End portion 62 prevents rotation of assembly 50 due to its three-faced construction (FIG. 7). Two of the three faces of end portion 62 are shown in FIG. 7 as faces 64. Each face 64 is substantially triangular in shape and is at an angle to each adjacent face. End portion 62 of pin 56 is sharpened to facilitate insertion into the bone.

In an alternative embodiment of attachment assembly 50, receiver holder 52 may have a two-part construction (not shown). The alternative receiver holder may have a first part that attaches directly to the patient's bone using bone screw 54 and a second part for holding receiver 16, 18 that snaps onto the first part. This allows the surgeon to remove the second part of the receiver holder during the procedure, thereby providing additional space for the surgeon to conduct the procedure. When the surgeon desires to take measurements of the relative position and orientation of the patient's bones using receiver 16, 18, the surgeon may snap the second part of the receiver holder back onto the first part.

Figure 8:
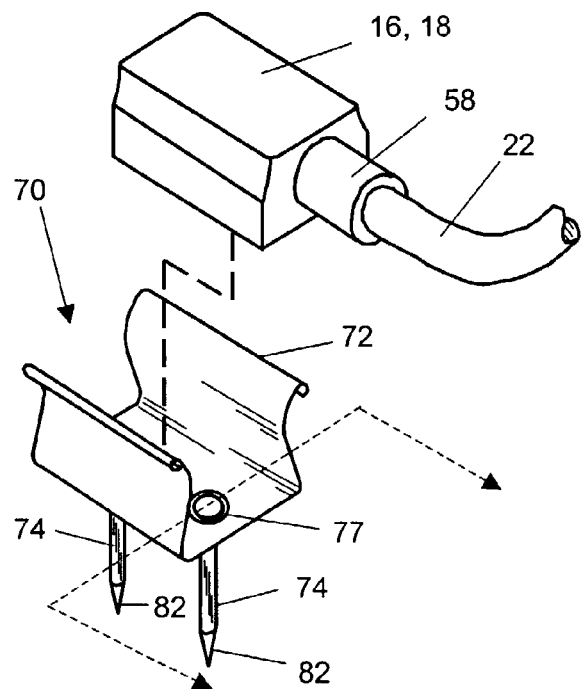
FIGS. 8–10 show other illustrative attachment apparatus suitable for attachment of a telemetry device to a patient in accordance with this invention.
Figure 9:
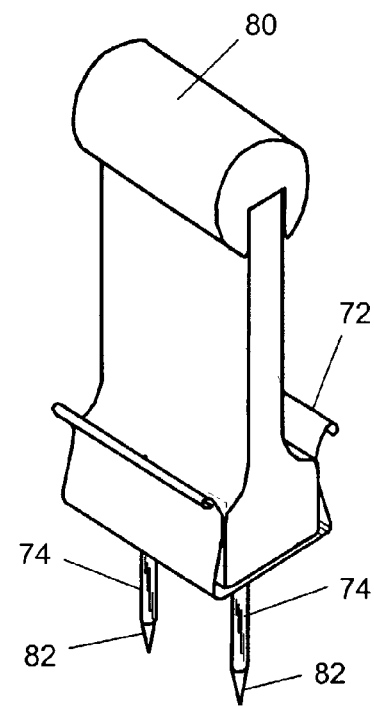
Figure 10:
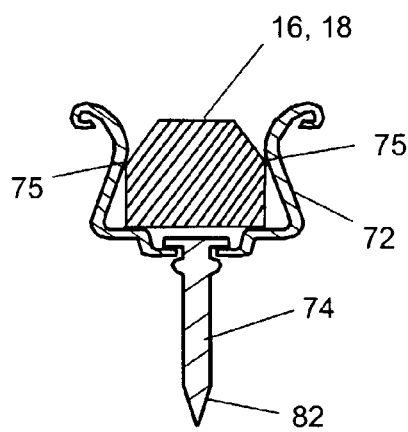

FIGS. 8–10 show other attachment apparatus suitable for attachment of positioning sensors, such as receiver 16, 18, to patient 10 (FIG. 1). As shown in FIG. 8, attachment assembly 70 includes receiver clip 72 and pins 74. Also shown in FIG. 8 is receiver 16, 18. Attached to receiver 16, 18 is wire sleeve 58, described hereinabove in connection with FIG. 4, that is used to house the end of wire 22 that attaches to the receiver.

Receiver clip 72 may be constructed of a rigid material such as, for example, a stainless steel, titanium, a plastic (e.g., polyethylene ("PE"), polyethylene terephthalate ("PET"), polypropylene ("PP"), polystyrene ("PS"), polycarbonate ("PC")), or any other suitable material. In embodiments of this invention that use electromagnetic telemetric position monitoring technology (e.g., electromagnetic receiver 16, 18), receiver clip 72 is preferably constructed of a non-magnetic material. Receiver 16, 18 is retained by receiver clip 72 for attachment to patient 10 (FIG. 1) by being "snapped" into place, as shown in FIG. 10. The force exerted on receiver 16, 18 by receiver clip 72, due to the interference fit 75 between the receiver and the receiver clip, retains the receiver in place (FIG. 10).

Pins 74 may be constructed of a metal such as a stainless steel or titanium. In embodiments of this invention that use electromagnetic telemetric position monitoring technology (e.g., electromagnetic receiver 16, 18), pins 74 are preferably constructed of a non-magnetic material. Pins 74 may be inserted into holes 77 for attachment of receiver clip 72 to a bone of patient 10 (FIG. 1). (It should be noted that while only one hole 77 is shown in receiver clip 72 (FIG. 8), there are actually two holes in the receiver clip. However, due to the angle at which receiver clip 72 is shown in FIG. 8, only one hole 77 is visible.) In some embodiments of this invention, pins 74 may be retained within holes 77 of receiver clip 72 so that the pins do not separate from assembly 70 during use in an orthopedic medical procedure. For example, a hole 77 may have a diameter that is slightly smaller than the diameter of the shaft of a pin 74, thereby creating an interference fit between the hole and the pin. In another example, a retaining clip may be used around the portion of the shaft of pin 74 that extends from receiver clip 72.

Driver 80, as shown in FIG. 9, may be used to drive assembly 70 into a bone of patient 10 (FIG. 1). End portions 82 of pins 74 are sharpened to facilitate insertion into the bone.

Figure 11:
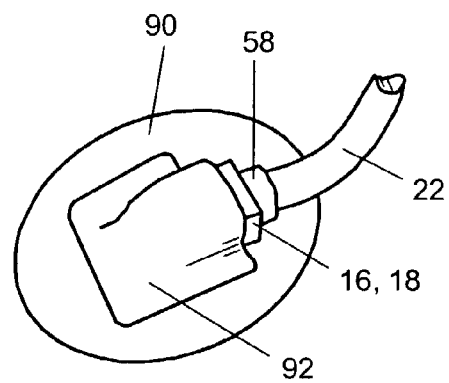
FIG. 11 shows still other illustrative attachment apparatus suitable for attachment of a telemetry device to a patient in accordance with this invention.

As shown in FIG. 11, a non-invasive approach of attaching receiver 16, 18 to patient 10 (FIG. 1) is provided by using an adhesive patch. Adhesive patch 90 is similar to, for example, the adhesive patches used to attach electrocardiogram electrodes to the chest of a patient. Adhesive patch 90 includes a receiver cover 92 that holds receiver 16, 18 to the surface of adhesive patch 90. Rather than being attached to a bone of patient 10, adhesive patch 90 is non-invasive in that it attaches to the skin of patient 10. For example, one adhesive patch may be placed on the skin of patient 10 near the iliac crest, and another adhesive patch may be placed on the skin of the patient on the anterior-facing portion of the knee.

Alternatively to the attachment apparatus described hereinabove in connection with FIGS. 4–11, receiver 16, 18 may be attached to patient 10 (FIG. 1) using commonly-known pins and/or wires (e.g., Kirschner wires, or "K" wires).

Figure 12:
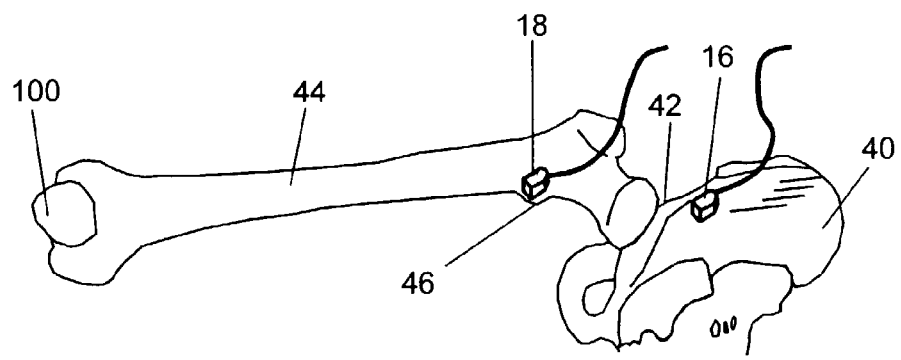
FIG. 12 is a schematic diagram of apparatus of FIG. 1 for making intraoperative orthopedic measurements showing an early stage in use of the apparatus in accordance with this invention.

FIG. 12 shows first electromagnetic receiver 16 and second electromagnetic receiver 18 as attached to pelvis 40 and femur 44, respectively, of patient 10 (FIG. 1). As mentioned hereinabove in reference to FIG. 2, prior to attachment of first electromagnetic receiver 16 to pelvis 40, but following attachment of second electromagnetic receiver 18 to femur 44, a reference direction may be established. To establish the reference direction, the surgeon may hold first electromagnetic receiver 16 at the base of kneecap 100. The recording of the reference direction data may be initiated by, for example, interaction with user interface 26 (FIG. 3). For example, the surgeon may press a button of user interface 26, indicating to processing device 14 that first electromagnetic receiver 16 is in place for determination of the reference direction. After the reference direction has been established, first electromagnetic receiver 16 is attached to pelvis 40 using the approaches described hereinabove.

With both of receivers 16 and 18 in place, as shown in FIG. 12, processing device 14 may receive an indication that the receivers are in place and that the bones (i.e., pelvis 40 and femur 44) are in their initial relative position and orientation. In other words, the hip joint is in its initial relative position and orientation, as it was prior to the start of the hip joint replacement procedure. The indication may be made by, for example, the surgeon's interaction with user interface 26 (FIG. 3). The surgeon may then articulate the leg of patient 10 (FIG. 1) through a range of motion. (Other than femur 44, the leg of patient 10 is not shown in FIG. 12. However, the leg of patient 10 is shown in full in FIG. 1. By articulating the leg of patient 10 through a range of motion, the surgeon is of course articulating femur 44 through the same range of motion.) As the surgeon articulates the leg through the range of motion, the positions of receivers 16 and 18 are recorded by processing device 14 (FIG. 3). Specifically, the positions of receivers 16 and 18 are communicated to processing device 14 via communication links 22 (i.e., wires 22). It is not necessary for the surgeon to articulate the leg through a predetermined path. However, it may be helpful for the surgeon to do so.

Figure 13:
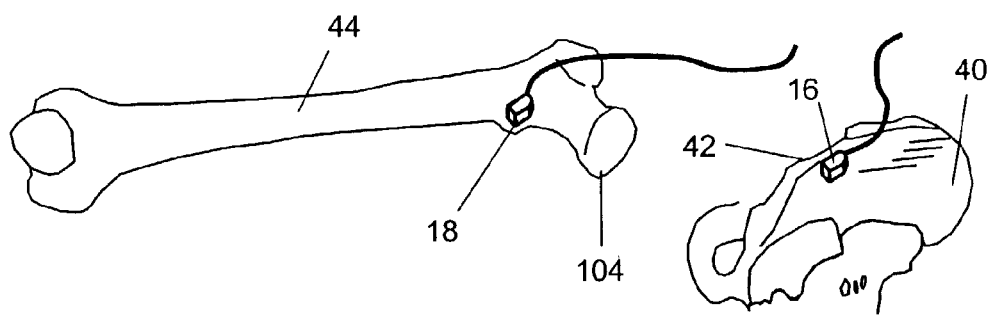
FIG. 13 is a view similar to FIG. 12 showing a later stage in use of the apparatus of FIG. 12 in accordance with this invention.

After the surgeon has articulated the leg, the surgeon may "dislocate the joint" (i.e., remove femur head 104 of femur 44 from the confines of acetabulum 42 of pelvis 40), as shown in FIG. 13. The surgeon may then, as in a typical hip joint replacement procedure, ream acetabulum 42 (if necessary) and install acetabular cup implant 102 in acetabulum 42. The surgeon may also, as in a typical hip joint replacement procedure, remove femoral head 104, broach the implant cavity in femur 44, and install femoral implant 106. Femoral implant 106 may be a "trial" femoral implant, in that the implant is used until the surgeon determines that the implant is of the correct length (as apparatus and methods of this invention address), at which point a final femoral implant is installed in the implant cavity.

Figure 14:
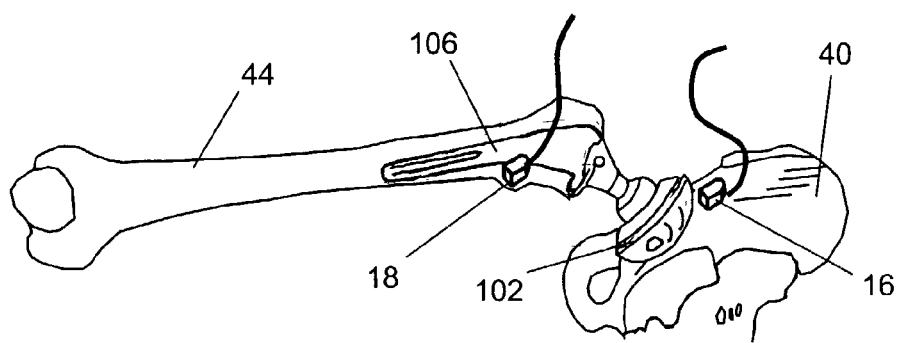
FIG. 14 is a view similar to FIG. 13, but showing additional apparatus, and showing a still later stage in use of the apparatus of FIG. 12 in accordance with this invention.

With acetabular implant 102 and trial femoral implant 106 in place, as shown in FIG. 14, processing device 14 (FIG. 3) may receive an indication that another relative position and orientation measurement is desired. The indication may be made by the surgeon's interaction with user interface 26 (FIG. 3). The surgeon may then articulate the leg of patient 10 (FIG. 1) through a range of motion. As the surgeon articulates the leg through the range of motion, the positions of receivers 16 and 18 are recorded by processing device 14. Specifically, the positions of receivers 16 and 18 are communicated to processing device 14 via communication links 22 (i.e., wires 22). Again, it is not necessary for the surgeon to articulate the leg through a predetermined path. However, it may be helpful for the surgeon to do so.

Measurement application 32 (FIG. 3) may determine the difference between the initial leg anatomy and the current leg anatomy (i.e., a differential measurement) based on the current relative position and orientation data communicated by receivers 16 and 18 to processing device 14, and based on the initial relative position and orientation data stored, for example, in memory 30 of processing device 14 (FIG. 3).

Referring back to FIG. 2, differential measurements, such as leg length difference 110 and offset 112, may be displayed graphically on display 24 of processing device 14. However, leg length difference 110 and offset 112 are just two possible differential measurements that may be displayed on display 24 for the surgeon, and any suitable differential measurement may be displayed. For example, acetabular cup implant orientation or range of motion may be displayed on display 24. Based on the information shown on display 24, the surgeon can decide whether the procedure will be successful using the component sizes chosen by the surgeon (e.g., acetabular cup implant 102 and femoral implant 106 of FIG. 14). If the information shown on display 24 is a result that is undesirable to the surgeon, the surgeon may make adjustments to, for example, the femoral implant, until the desired anatomy is achieved. Once the desired anatomy is achieved, a final femoral implant is inserted into the femoral implant cavity, and the hip joint is "reduced" (i.e., the final femoral implant is attached to acetabular cup implant 102). To ensure proper relative position and orientation of the final prosthesis (i.e., the assembly of the final femoral implant and acetabular cup implant 102), final differential measurements may be determined using the apparatus and methods of this invention described hereinabove.

Figures 15, 16:
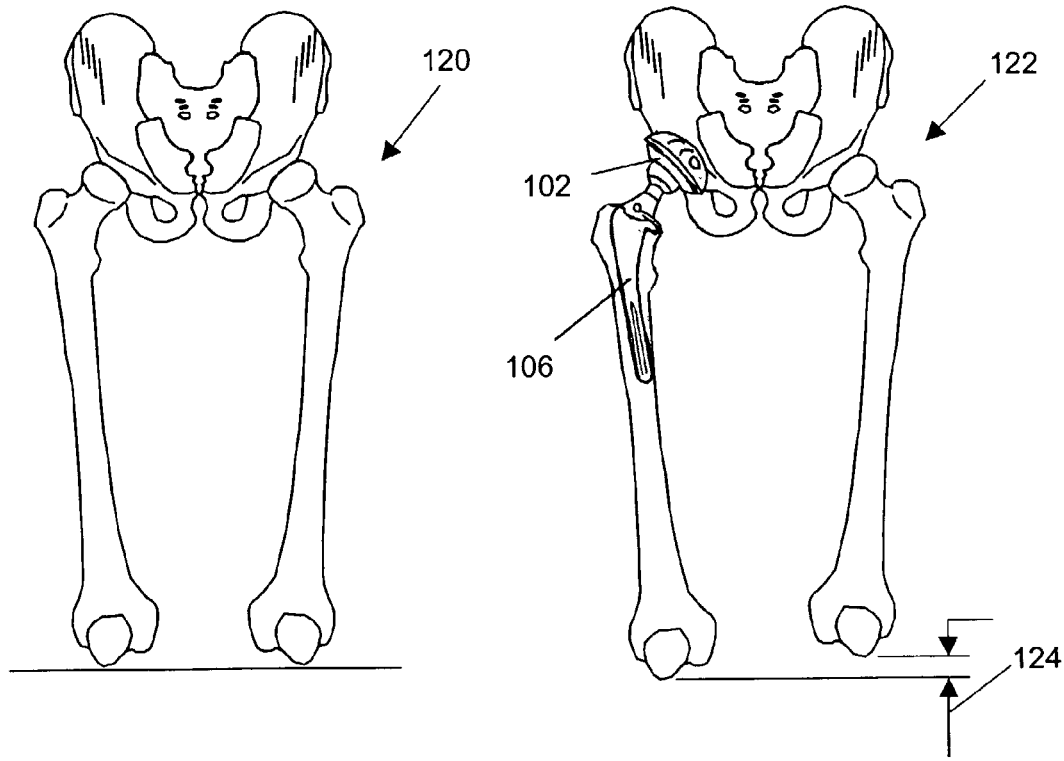
FIGS. 15–17 show an illustrative example of a leg length difference differential measurement in a hip joint replacement procedure in accordance with this invention.
Figure 17:
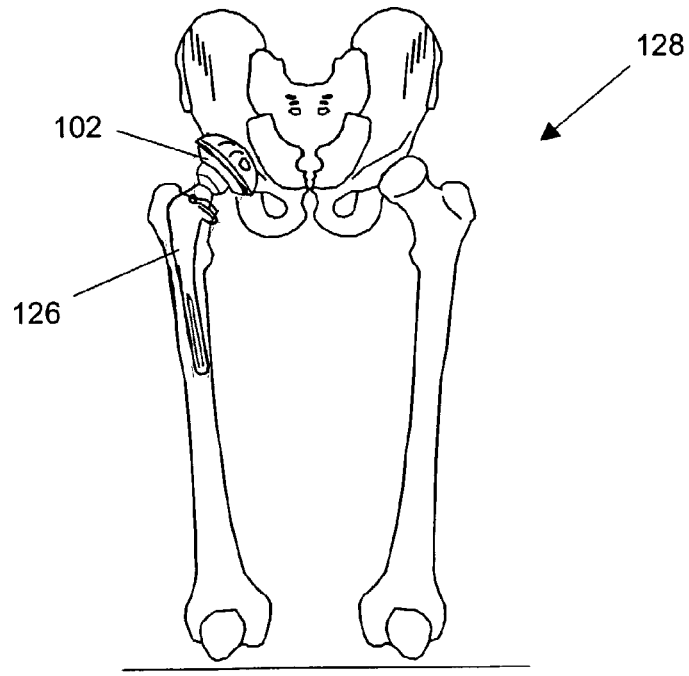

As mentioned hereinabove, the surgeon may review a differential measurement in connection with leg length difference. For purposes of illustration, and in connection with both the leg length difference differential measurement and other differential measurements, an example involving leg length difference is shown in FIGS. 15–17. In this example, it is assumed that the surgeon desires the patient (e.g., patient 10 (FIG. 1)) to have the same leg length with the replacement hip joint as with the patient's natural hip joint. FIG. 15 shows a preoperative condition 120 of the patient, in which the patient's legs are of equal length. (Other than the femurs, the legs of the patient are not shown in FIGS. 15–17. However, the leg length difference demonstrated by the femurs of the patient is representative of the actual leg length difference of the patient.) FIG. 16 shows an intraoperative condition 122, which involves the patient at some point during the hip joint replacement procedure, after acetabular cup implant 102 and trial femoral implant 106 have been installed in the patient. A differential measurement (e.g., leg length difference) in connection with intraoperative condition 122 of the patient may show that there is a leg length difference 124 between preoperative condition 120 (FIG. 15) and intraoperative condition 122. This leg length difference value 124 may be displayed, for example, on display 24 (FIG. 2). The surgeon, upon reviewing the leg length difference value 124, and with the goal of returning the patient to his or her initial, preoperative anatomy (i.e., preoperative condition 120), may alter the anatomy of the hip joint prosthesis. For example, if leg length difference 124 is a value of 1.5 cm (i.e., the patient's leg with the prosthesis is 1.5 cm longer than the patient's leg without the prosthesis), the surgeon may replace acetabular cup implant 102 with an implant that is 1.5 cm shorter. Alternatively, the surgeon may replace trial femoral implant 106 with a femoral implant that is 1.5 cm shorter. As shown in FIG. 17, the surgeon has replaced trial femoral implant 106 with a final femoral implant 126 that is 1.5 cm shorter than the trial femoral implant, thereby bringing the patient to a postoperative condition 128 that is identical to the patient's initial, preoperative anatomy (i.e., preoperative condition 120).

As described hereinabove in the previous example, it is typically the case that a surgeon desires to restore a patient to his or her preoperative anatomy. However, in some cases, joint disease may create a need to lengthen a patient's leg or to otherwise alter the patient's preoperative anatomy with a prosthesis. In such a case, the surgeon may determine preoperatively, for example, that a patient's leg needs to be lengthened by a certain amount. The surgeon may make such a preoperative determination using any typical preoperative planning method for a hip joint replacement procedure. One typical preoperative planning method used in conjunction with a hip joint replacement procedure involves taking an x-ray of a patient's anatomy prior to the procedure. The surgeon may use templates of implant components (e.g., a femoral implant and an acetabular cup implant) and may attempt to "fit" these templates onto the x-ray of the patient's anatomy to determine the proper trial components to use in the procedure. (It should be noted that trial prosthetic components are also described hereinabove in connection with FIGS. 12–14.) Apparatus and methods of this invention can be used to achieve the surgeon's goal of altering the patient's preoperative anatomy with a prosthesis.

In order to determine the relative position and orientation of a patient's bones and/or prosthesis, and to determine differential measurements based on the relative position and orientation information, processing device 14 implements measurement application 32, which may be stored in memory 30 of the processing device (FIG. 3). Measurement application 32 may perform various algorithms to determine, for example, the relative positions and orientations of the patient's bones and/or prosthesis and the differential measurements. For purposes of illustration, various examples of algorithms performed by measurement application 32 are described hereinbelow in reference to FIGS. 18–26. (Flow charts of illustrative steps involved in performance of the various algorithms by measurement application 32 are provided in FIGS. 27–34.) The algorithm examples are provided in connection with a hip joint replacement procedure. These examples are in no way a limitation of the capabilities of measurement application 32, as measurement application 32 may be capable of performing any suitable algorithm in connection with intraoperative measurements in any orthopedic medical procedure.

To better appreciate the following examples, some reference characters used throughout both the textual descriptions of the examples of algorithms and the related FIGS. are provided hereinbelow in the "Table of Definitions."

TABLE OF DEFINITIONS

| | |
|---|---|
| $C_F$ | Point located at a set distance, $\Delta_S$, from the end of the femur sensor. The point is roughly centered in the femur shaft. |
| $C_J$ | XYZ-coordinates location of center of rotation of the hip joint in the pelvis reference frame, P. |
| F | Femur reference frame, as defined by the XYZ-coordinates and angle matrix of the femur sensor (i.e., femur sensor 18), in the absolute reference frame (i.e., the reference frame of the magnetic field generator). |
| $F_P$ | XYZ-coordinates location and angle matrix orientation of the femur sensor (i.e., femur sensor 18) relative to the pelvis reference frame, P. |
| $K_F$ | XYZ-coordinates location of the knee relative to the femur reference frame, F. |
| $K_P$ | XYZ-coordinates location of the knee relative to the pelvis reference frame, P. |
| $L_F$ | Leg length measurement. |
| $O_F$ | Femur offset, as defined by the distance from $V_F$ to $C_J$ that is perpendicular to $V_F$. |
| $O_P$ | Pelvis offset, as defined by the distance between P to $C_J$, projected onto $V_O$. |
| P | Pelvis reference frame, as defined by the XYZ-coordinates and angle matrix of the pelvis sensor (i.e., pelvis sensor 16), in the absolute reference frame (i.e., the reference frame of the magnetic field generator). |
| $V_F$ | Vector defining the center of the femur shaft. This vector passes through $K_P$ and $C_F$. |
| $V_L$ | Vector defining the leg length direction. This vector passes through $C_J$ and $K_P$ while the patient's legs are in a standing position. If the patient were standing, $V_L$ would typically be vertical. |
| $V_O$ | Vector defining the offset direction. This vector passes through $C_J$ and is perpendicular to $V_F$. |

-continued

TABLE OF DEFINITIONS

| | |
|---|---|
| $V_P$ | Vector about which flexion occurs. This vector is constructed perpendicularly to $V_L$, through $C_J$, and intersecting $V_F$. |
| α | Internal/external rotation angle of the leg about $V_L$. |
| $A_S$ | Assumed distance from the femur sensor (i.e., femur sensor 18) to the center of the femur shaft. |
| Φ | Abduction angle about an axis perpendicular to $V_P$ and $V_L$ and passing through $C_J$. |
| ρ | 3-D angle between $V_L$ and $V_L'$. |
| Θ | Flexion/extension angle about $V_P$. |

Figure 18:
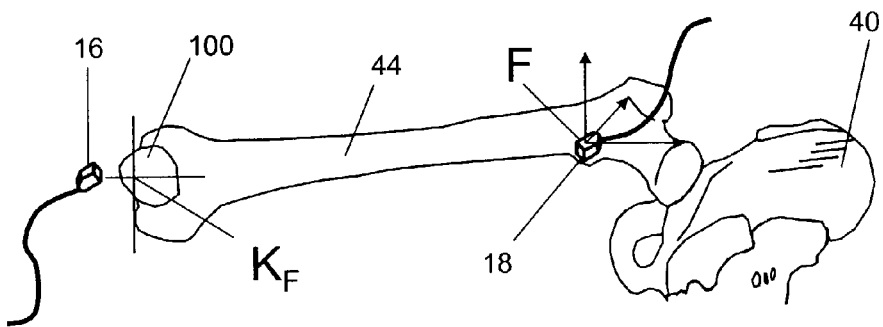
FIGS. 18–26 show illustrative examples of various algorithms performed by a measurement application in connection with a hip joint replacement procedure in accordance with this invention.

FIG. 18 illustrates the recording of a reference direction by measurement application 32 (FIG. 3). (It should be noted that the recording of a reference direction is also described hereinabove in reference to FIG. 12.) (Illustrative steps involved in the recording of a reference direction by measurement application 32 are provided, for example, in the flowchart of FIGS. 27 and 28 and, specifically, in FIG. 27.) After second electromagnetic receiver 18 (which may be referred to hereinafter as both "femur sensor 18" and "receiver 18," interchangeably) has been attached to femur 44, first electromagnetic receiver 16 (which may be referred to hereinafter as both "pelvis sensor 16" and "receiver 16," interchangeably) is held against kneecap 100 to record $K_F$. $K_F$ is the XYZ-coordinates location of the patient's knee in the femur reference frame, F. Femur reference frame, F, is the reference frame of femur sensor 18 in the absolute reference frame (i.e., the reference frame of magnetic field generator 20 (FIG. 2)). Thus, in the arrangement of sensors 16 and 18 shown in FIG. 18, measurement application 32 determines $K_F$. The location of $K_F$ may be stored for later use (e.g., in memory 30 of FIG. 3).

Figure 19:
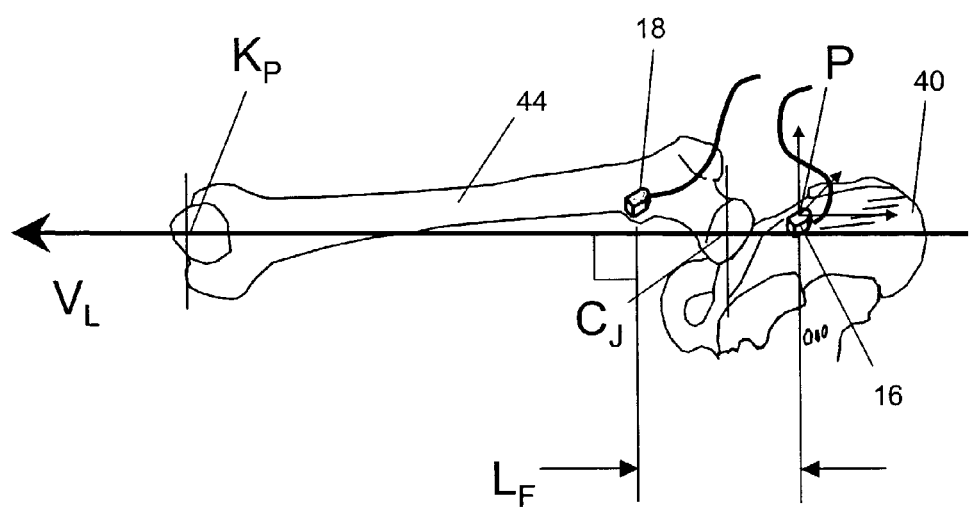
Figure 27:
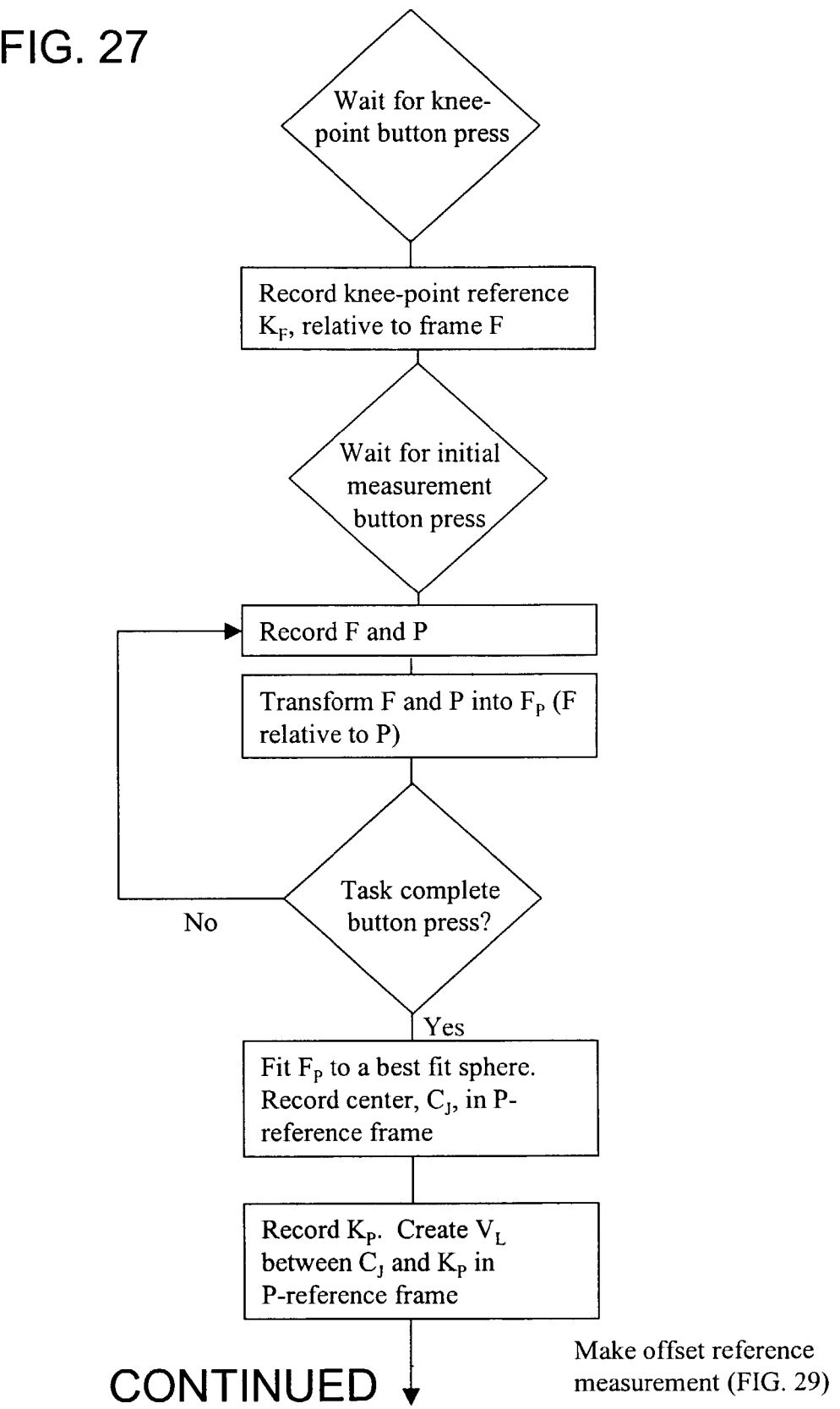
Figure 28:
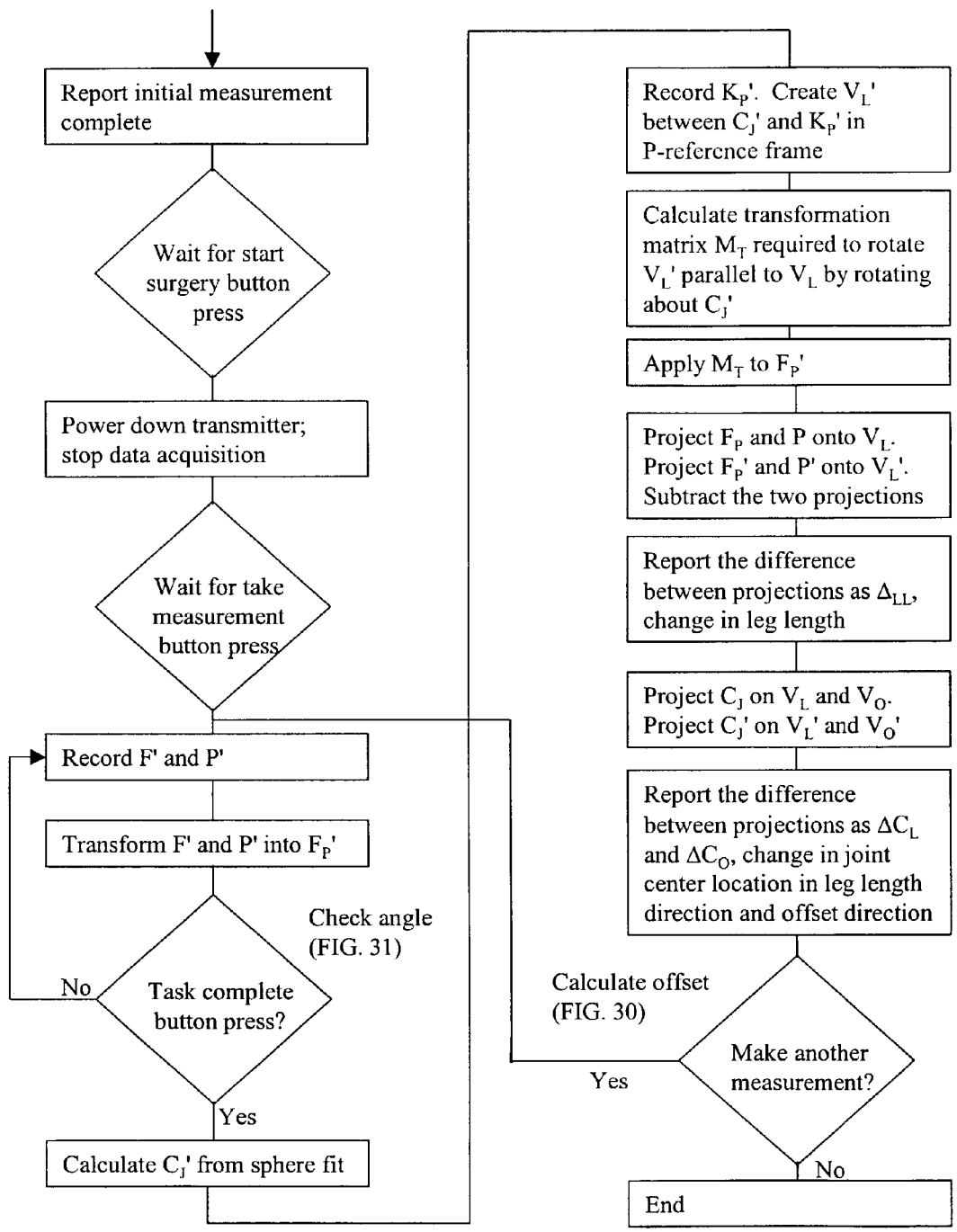
Figure 31:
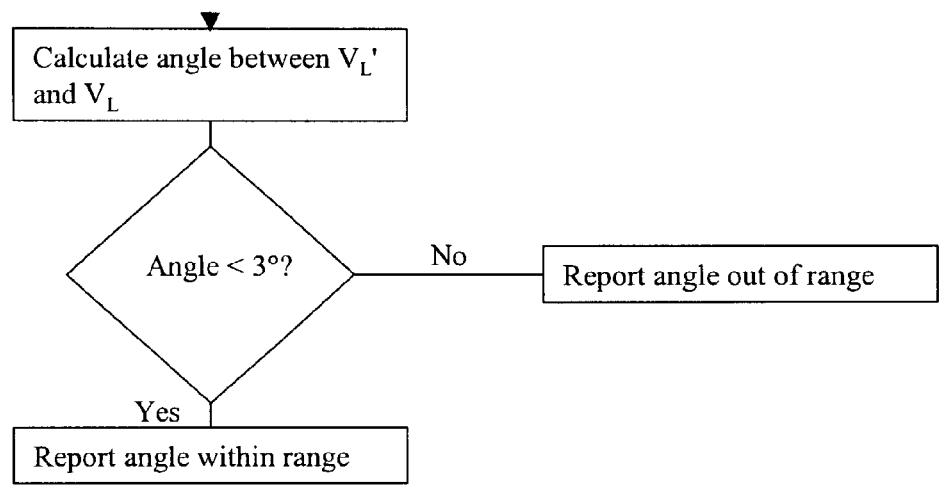
Figure 32:
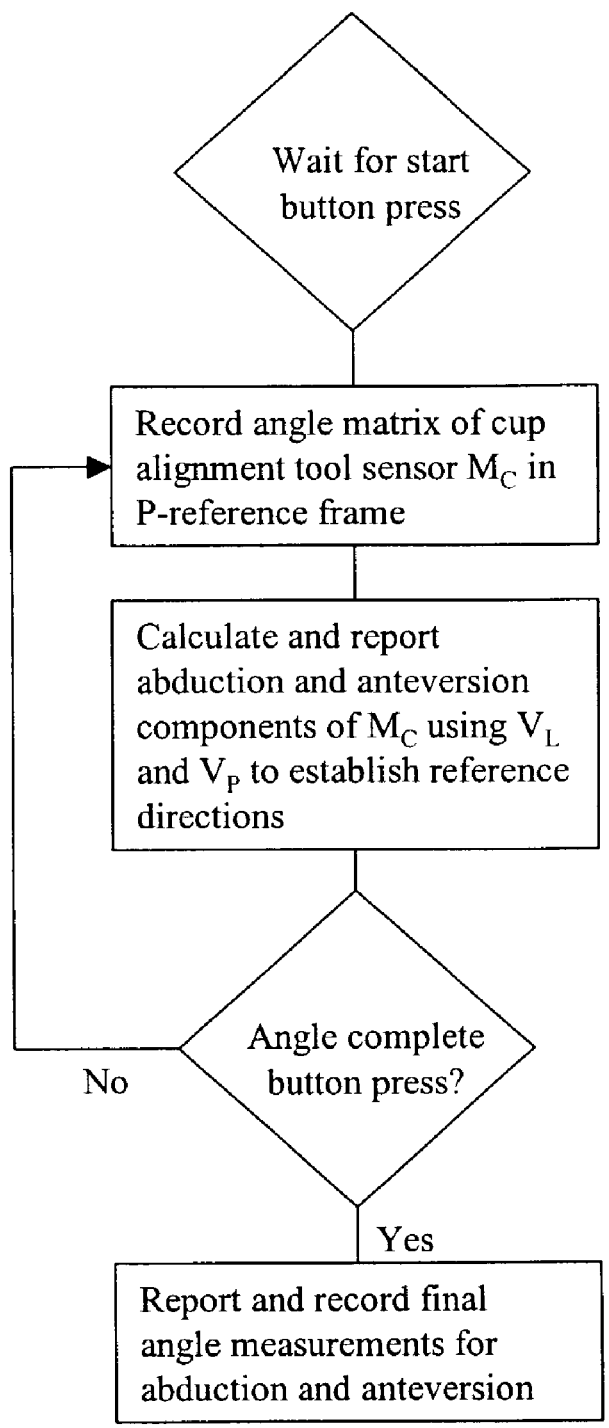
Figure 33:
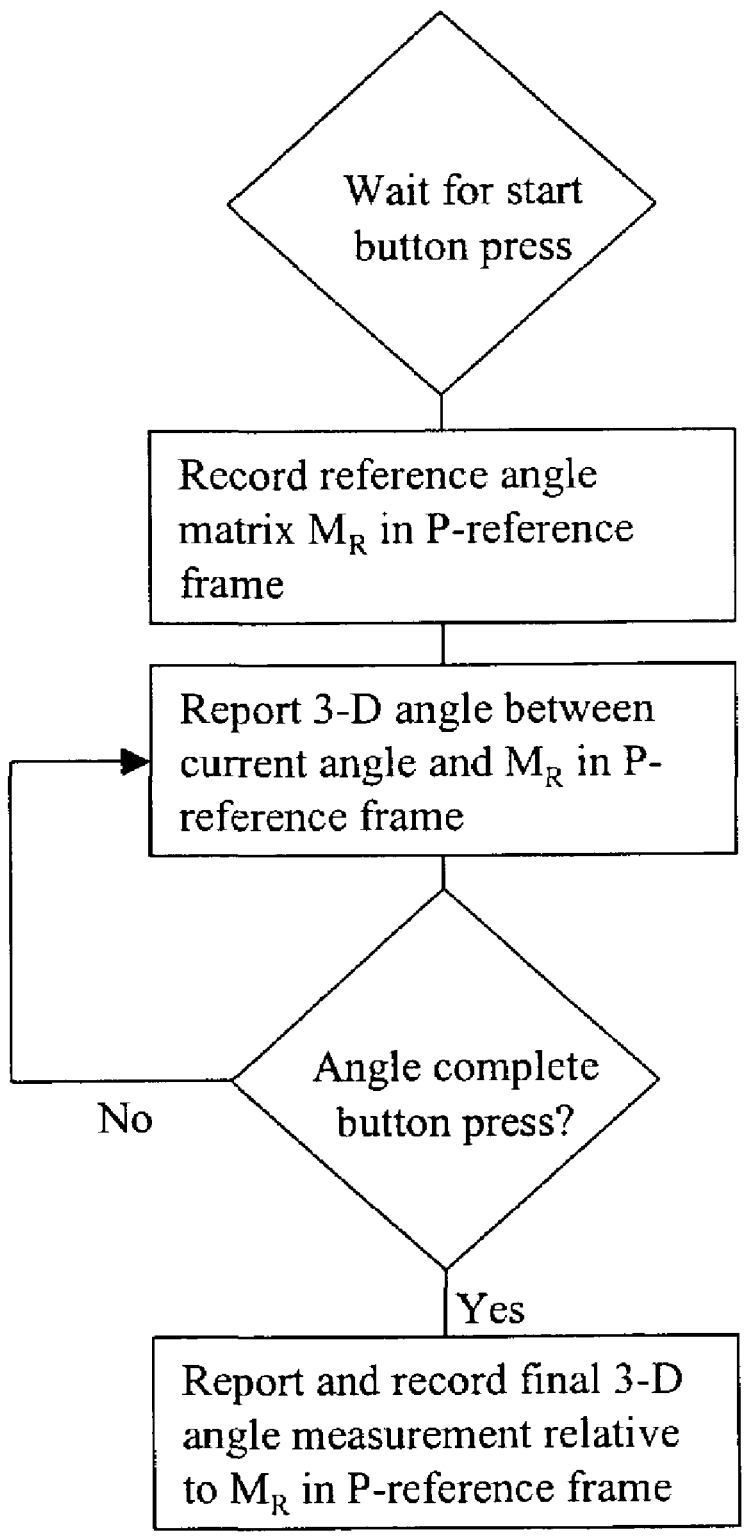
Figure 34:
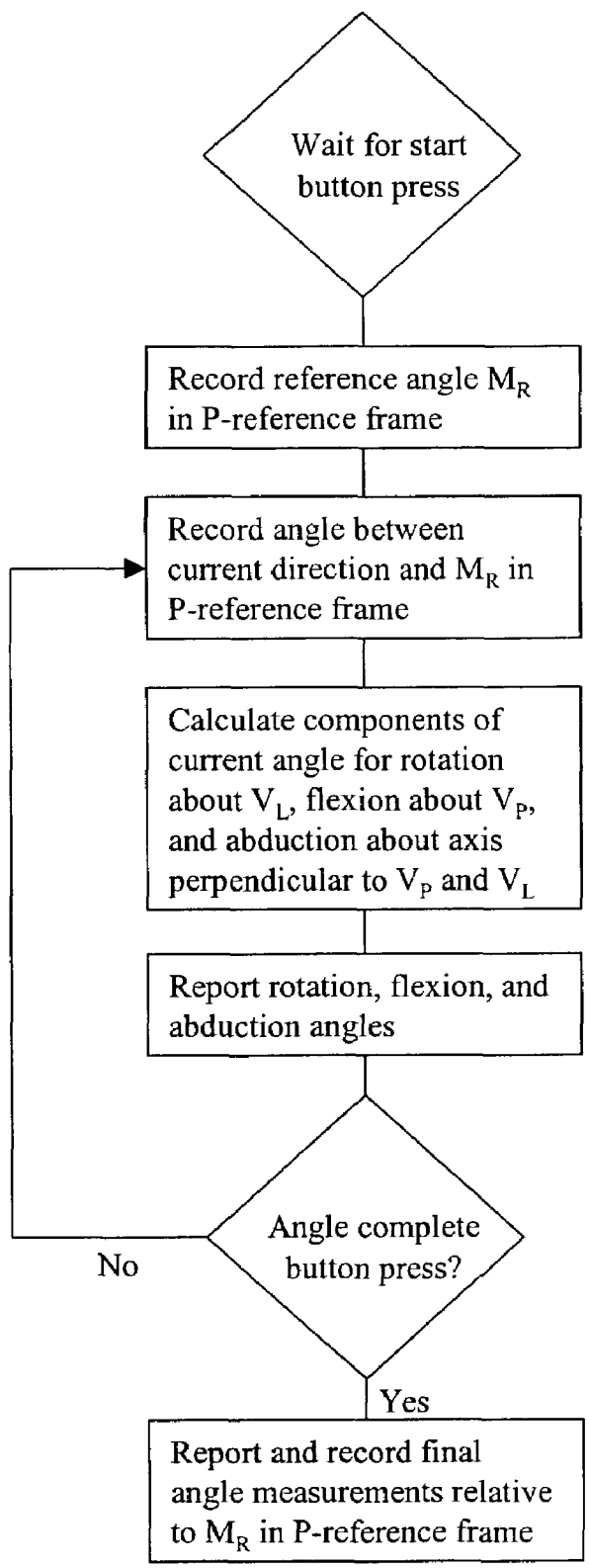

FIG. 19 illustrates the recording of an initial leg length measurement, $L_F$, by measurement application 32 (FIG. 3) (Illustrative steps involved in the recording of an initial leg length measurement by measurement application 32 are provided, for example, in the flowchart of FIGS. 27 and 28.) Measurement application 32 records $C_J$, the center of rotation of the patient's natural hip joint, by fitting a sphere to the position and orientation data communicated from sensors 16 and 18 to processing device 14 (FIG. 3). The data communicated from receivers 16 and 18 is communicated to processing device 14 as the surgeon takes the patient's leg through a range of motion. Measurement application 32 defines a leg length vector, $V_L$, by taking a vector through points $C_J$ and $K_P$. Measurement application 32 determines the initial leg length measurement, $L_F$, by projecting femur sensor 18 and pelvis sensor 16 onto $V_L$ and taking the distance between the projected points. This distance, $L_F$, may be stored for later use (e.g., in memory 30 of FIG. 3).

Figure 20:
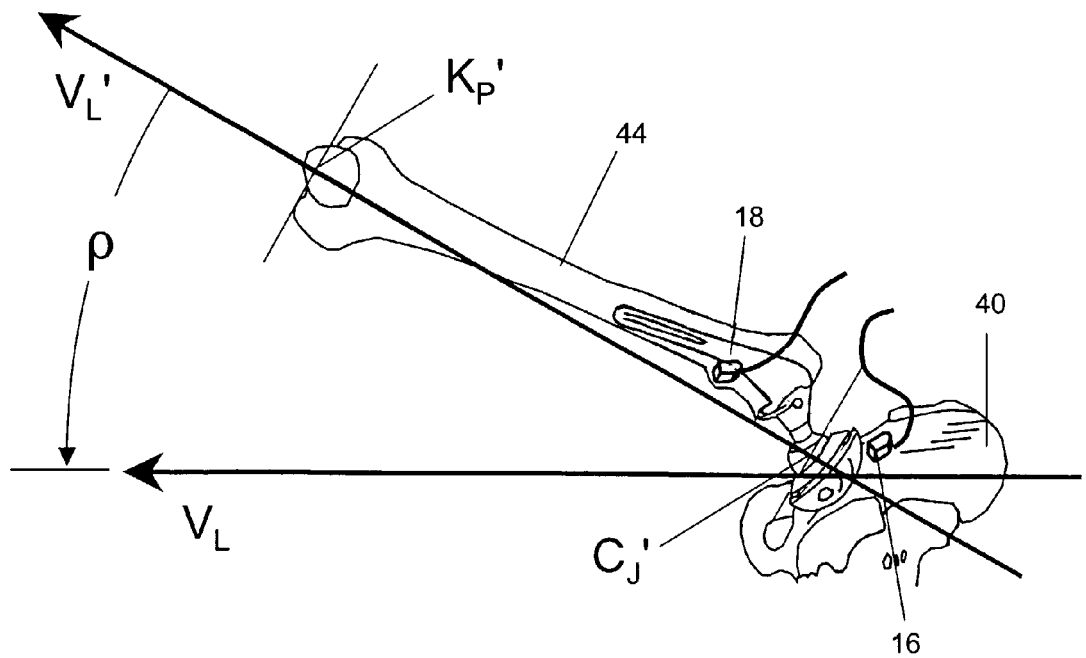

FIG. 20 illustrates the transformation performed by measurement application 32 (FIG. 3) for determination of an intraoperative leg length measurement (i.e., after installation of the hip joint prosthesis). This transformation allows the leg length measurement to be accurate regardless of the angle that a patient's leg is left in by the surgeon during the measurement. (Illustrative steps involved in the transformation performed by measurement application 32 for determination of an intraoperative leg length measurement are provided, for example, in the flowchart of FIGS. 27 and 28 and, specifically, in FIG. 28.) As shown in FIG. 20, this measurement is made at some time during the hip joint replacement procedure after both the dislocation of the hip joint and the insertion of the hip joint prosthesis. As described hereinabove, the prosthesis inserted in the patient may consist of trial components until the surgeon has made the determination that the components are of an appropriate size. As used herein, "prime notation," signified by a single quote ('), refers to any measurement made after the installation of a prosthesis. For example, $V_L$ is an initial vector defining the leg length direction, while $V_L'$ is a vector defining the leg length direction at some time after the installation of the prosthesis.

Measurement application 32 (FIG. 3) uses ρ, which is the angle between $V_L$ and $V_L'$, and $C_J'$, which is the center of rotation of the prosthetic joint, to determine a transformation matrix, $M_T$. In some embodiments of this invention, measurement application 32 may require that ρ fall within a certain range of values. For example, as provided in the flowchart of FIG. 31, measurement application 32 may determine whether the angle between $V_L'$ and $V_L$ (i.e., ρ) is within a proper range of values (e.g., less than 3 degrees). If ρ is not within the proper range, measurement application 32 may cause an indication regarding the improper range to be displayed on display 24 of processing device 14 (FIG. 3). Measurement application 32 applies $M_T$ to F' (i.e., the position of femur sensor 18 as projected onto $V_L'$) to "rotate" the patient's leg about $C_J'$ back to its initial positioning, parallel with $V_L$.

Figure 21:
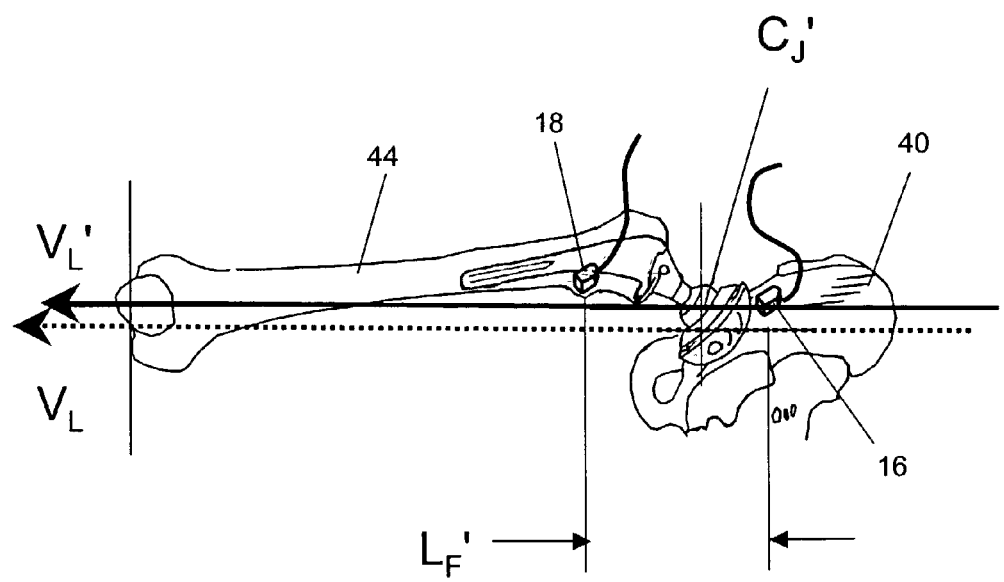

FIG. 21 shows the result of the transformation using $M_T$, in which measurement application 32 (FIG. 3) has transformed $V_L'$ such that it is parallel to $V_L$. As described hereinabove in connection with the initial leg length measurement (FIG. 19), measurement application 32 projects F' and P' onto $V_L'$ and calculates the distance between F' and P', which is $L_F'$. Using $L_F$ and $L_F'$, measurement application 32 calculates the leg length difference $\Delta_{LL}$:

$$\Delta_{LL}=L_F'-L_F$$

As described hereinabove in reference to FIG. 2, measurement application 32 may cause the leg length difference $\Delta_{LL}$ to be displayed on display 24 of processing device 14.

Figure 22:
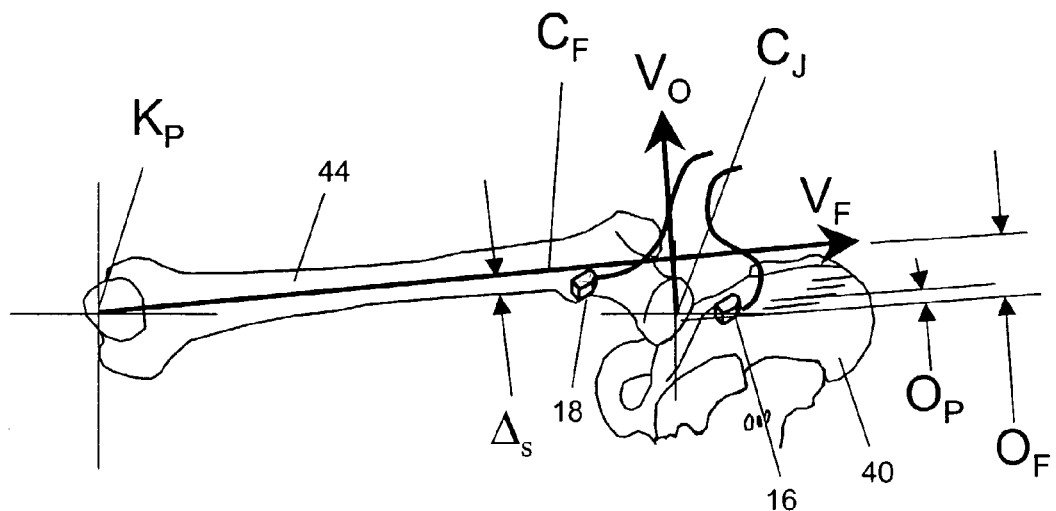

FIG. 22 illustrates the determination of "offset," which is defined as the perpendicular distance from the center of a patient's femur shaft to the center of rotation of the patient's hip joint, by measurement application 32 (FIG. 3). (Illustrative steps involved in the determination of offset by measurement application 32 are provided, for example, in the flowchart of FIGS. 27 and 28. As indicated in the flowchart of FIGS. 27 and 28, the flowcharts of both FIG. 29 and FIG. 30 also provide illustrative steps involved in the determination of offset.) Measurement application 32 determines the center of femur shaft 44 by assuming a femur radius, $A_s$, and by creating a point, $C_F$, at a distance of the assumed radius from femur sensor 18. Measurement application 32 constructs vector $V_F$ through $K_P$ and $C_F$, and, using $V_F$, the measurement application determines femur offset $O_F$ and pelvis offset $O_P$. $O_F$ is the perpendicular distance from $C_J$ to $V_F$. $O_P$ is the distance between pelvis sensor 16 and $C_J$, projected onto $V_O$. Using $O_F$ and $O_P$, measurement application 32 may determine the initial offset measurement as the sum of $O_F$ and $O_P$, known as $O_{total}$. The initial offset measurement may be stored for later use in memory 30 (FIG. 3).

Figure 23:
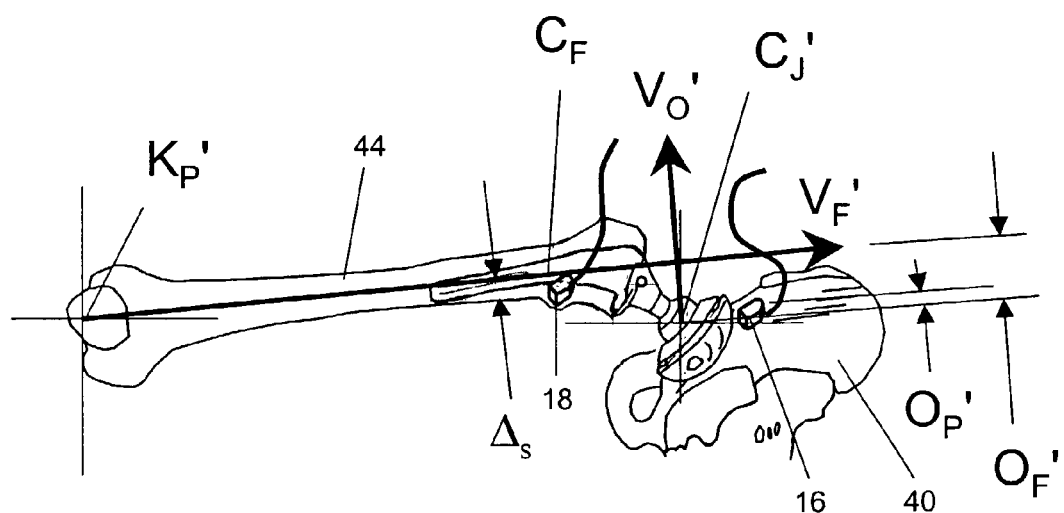

As shown in FIG. 23, measurement application 32 (FIG. 3 ) may determine an offset differential measurement at some time during the hip joint replacement procedure after both the dislocation of the hip joint and the insertion of the prosthesis. As described hereinabove, the prosthesis inserted in the patient may consist of trial components until the surgeon has made the determination that the components are of an appropriate size. As described hereinabove in connection with FIG. 20, measurement application 32 determines a transformation matrix $M_T$ and applies $M_T$ to $V_F'$ to rotate $V_F'$ so that it is parallel with $V_F$. Using $O_F'$ and $O_P'$, measurement application 32 may determine the offset as the sum of $O_F'$ and $O_P'$, also known as $O'_{total}$. (Measurement application 32 determines $O_F'$ and $O_P'$ using the same procedure as described hereinabove in connection with $O_F$ and $O_P$.) Using $O_{total}$ and $O'_{total}$, measurement application 32 calculates the offset difference $\Delta_O$:

$$\Delta_O = O'_{total} - O_{total}$$

As described hereinabove in reference to FIG. 2, measurement application 32 may cause the offset difference $\Delta_O$ to be displayed on display 24 of processing device 14.

Figure 24:
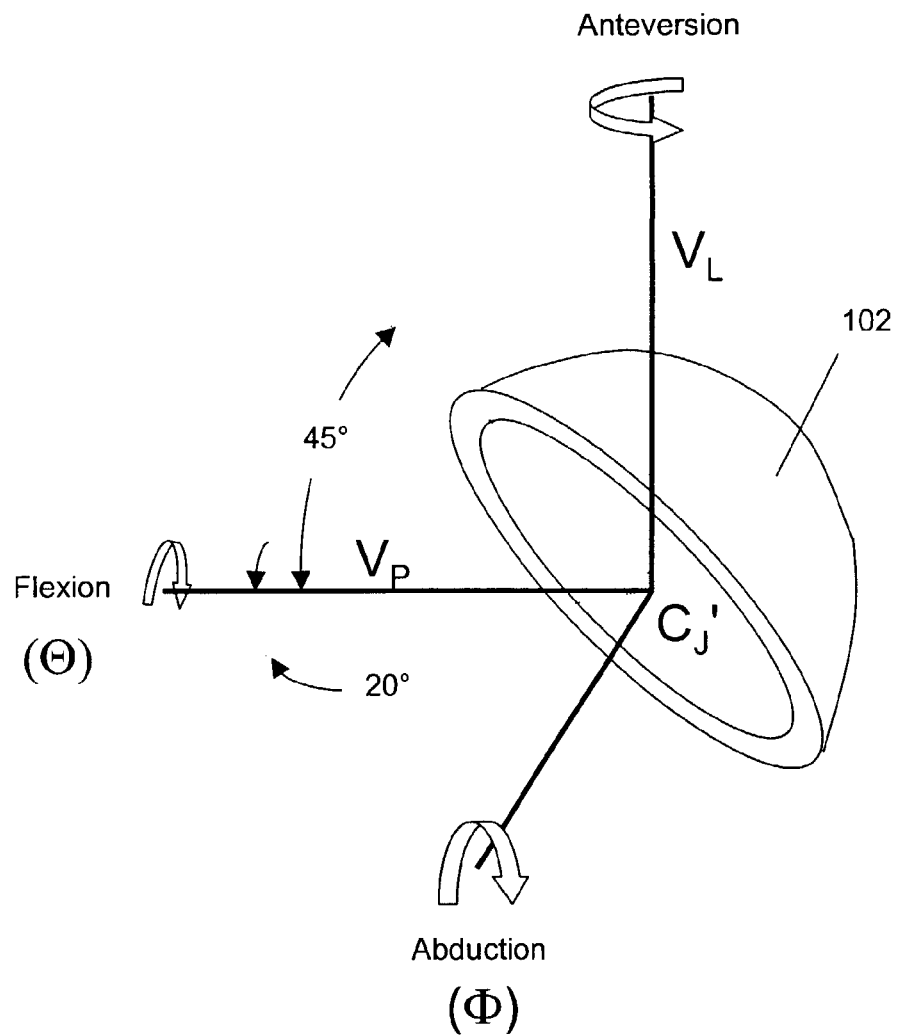

FIG. 24 illustrates how measurement application 32 (FIG. 3) determines an angle of installation of an acetabular cup implant in a patient. (Illustrative steps involved in the determination of an angle of installation of an acetabular cup implant by measurement application 32 are provided, for example, in the flowchart of FIG. 32.) As described hereinabove in reference to FIG. 14, an acetabular cup implant 102 may be installed in a patient by a surgeon. The ideal angle of installation, or angular orientation, of acetabular cup implant 102 is at about 45 degrees abduction and about 20 degrees anteversion. ("Abduction" is the angle that a patient's leg makes with respect to the patient's body when the patient lifts the leg out to the side. "Anteversion" is rotation about the vertical axis, $V_L$, with the patient in the standing position. "Flexion" is the angle that a patient's leg makes with respect to the patient's body when the patient kicks the leg forward.) This angular orientation of acetabular cup implant 102 is a "rule of thumb" for a surgeon to use in a patient to prevent dislocation of the prosthetic hip joint. However, this angular orientation is merely illustrative, and a surgeon can install an acetabular cup implant at any suitable orientation to prevent dislocation or to address any other concern in connection with the prosthetic hip joint.

To measure the angular orientation of acetabular cup implant 102, the surgeon may attach a telemetry device (not shown) to the implant. The surgeon may attach the telemetry device to acetabular cup implant 102 using, for example, any of the apparatus for attachment described hereinabove in reference to FIGS. 4–11. Measurement application 32 (FIG. 3), using $V_L$ as the anteversion reference direction and $V_P$ as the flexion reference direction, determines the abduction reference direction. (It should be noted that, although acetabular cup implant 102 has been installed in the patient, the trial femoral implant (e.g., trial femoral implant 106) has not yet been installed in the patient. Thus, the axes provided (i.e., axes $V_L$ and $V_P$) are shown as "initial" axes, prior to installation of the entire prosthetic hip joint.) Measurement application 32 may then cause some or all of the anteversion, flexion, and abduction angles of acetabular cup implant 102, with respect to the various reference directions, to be displayed on, for example, display 24 (FIG. 2).

In an alternative approach to determining the reference directions (i.e., anteversion, flexion, and abduction reference directions), the surgeon may use a stylus-equipped sensor to digitize known geometry of the patient's bone structure. Measurement application 32 (FIG. 3) may then develop reference directions based on the locations of certain bone features. For example, most patient's have certain "prominent anatomy," such as, for example, the top of the patient's iliac crest. By digitizing points along the top of the iliac crest, the surgeon provides measurement application 32 with sufficient points to create a plane through the points. The reference directions are then determined by measurement application 32 as vectors at certain angles to the plane.

Figure 25:
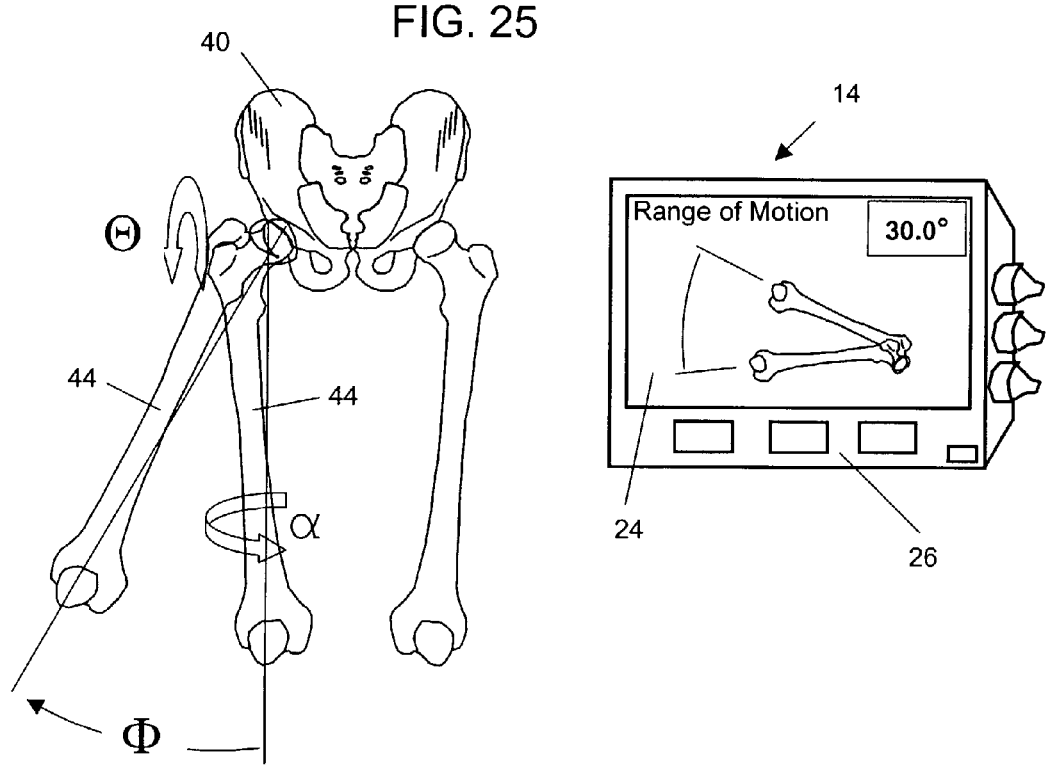
Figure 26:
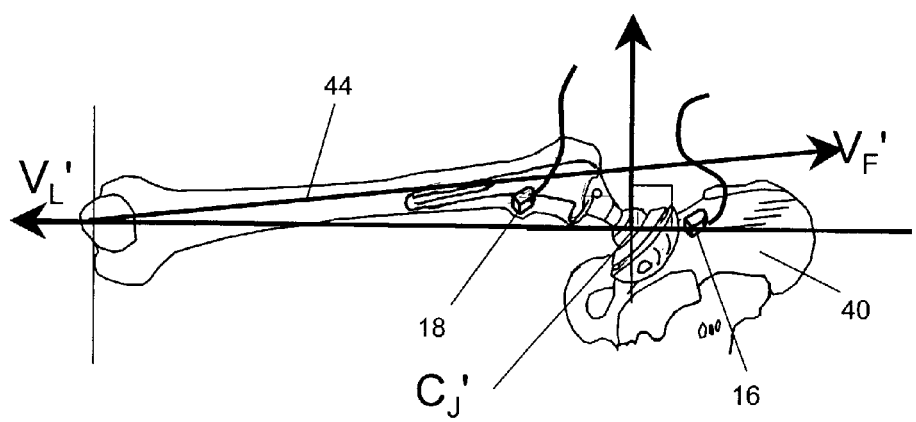

FIGS. 25–26 illustrate how measurement application 32 (FIG. 3) determines a range of motion differential measurement in a patient. One possible method that a surgeon may employ to provide measurement application 32 with information in connection with the range of motion differential measurement may be called the "3-D angle method." (Illustrative steps involved in performance of the 3-D angle method by measurement application 32 are provided, for example, in the flowchart of FIG. 33.) In the 3-D angle method, as illustrated in FIG. 25, the surgeon first sets the zero point for the 3-D angle. For example, the surgeon may interact with user interface 26 of processing device 14 (also shown in FIG. 3), thereby indicating to measurement application 32 the zero point for the angle. This zero point may be stored, for example, in memory 30 (FIG. 3) for later use by measurement application 32. The surgeon then articulates the patient's leg through a range of motion. As the leg is articulated, measurement application 32 calculates the 3-D angle of the leg using the zero point for reference. Measurement application 32 may cause this 3-D angle to be displayed, for example, on display 24. (It should be noted that, although the example of FIG. 25 is shown prior to the installation of the prosthesis, the same procedure can be employed by measurement application 32 after the installation of the prosthesis to determine a range of motion differential measurement.)

Another possible method that a surgeon may employ to provide measurement application 32 (FIG. 3) with information in connection with the range of motion differential measurement is by using reference directions, as described hereinabove in connection with other differential measurement algorithms (e.g., leg length difference, offset, and acetabular cup implant orientation). (Illustrative steps involved in the use of reference directions by measurement application 32 in range of motion measurements are provided, for example, in the flowchart of FIG. 34.) As illustrated in FIG. 26, measurement application 32 determines the reference directions about which the hip joint rotates, which are $V_L'$, $V_P'$, and the axis perpendicular to $V_L'$ and $V_P'$. (It should be noted that, although the example of FIG. 26 is shown after the installation of the prosthesis, the same procedure can be employed by measurement application 32 before the installation of the prosthesis to determine a range of motion differential measurement.) As stated hereinabove, anteversion is about $V_L'$ with the patient in the standing position, flexion is about $V_P'$, and abduction is about the axis perpendicular to $V_L'$ and $V_P'$. In this method, the surgeon again sets the zero point for the three reference directions. For example, the surgeon may interact with user interface 26 of processing device 14 (FIG. 3), thereby indicating to measurement application 32 the zero point for the angle. This zero point may be stored, for example, in memory 30 (FIG. 3) for later use by measurement application 32. The surgeon then articulates the patient's leg through a range of motion. As the leg is articulated, measurement application 32 calculates angles with respect to the three reference directions, using the zero point for reference. Measurement application 32 may cause these three angles to be displayed, for example, on display 24 (FIG. 3).

Thus, apparatus and methods for making intraoperative orthopedic measurements are provided. One skilled in the art will realize that the present invention can be practiced by other than the described embodiments, which are presented for purposes of illustration and not of limitation, and that the present invention is limited only by the claims which follow.

What is claimed is:

1. A method for making orthopedic measurements during an orthopedic medical procedure, the method comprising:
attaching a plurality of telemetry devices to a patient's body;
prior to a first portion of the orthopedic medical procedure, while moving the patient's body through a first range of motion, tracking movement of the plurality of telemetry devices relative to each other, and calculating the position of at least one anatomical feature of the patient's body relative to the plurality of telemetry devices based on the movement of the plurality of telemetry devices;
after the first portion of the orthopedic medical procedure, while moving the patient's body through a second range of motion, tracking movement of the plurality of telemetry devices relative to each other, and calculating the position of the at least one anatomical feature relative to the plurality of telemetry devices based on the movement of the plurality of telemetry devices; and
determining a differential measurement in connection with the first portion of the orthopedic medical procedure, wherein the differential measurement is based at least in part on the calculated position of the at least one anatomical feature before the first portion of the orthopedic medical procedure and on the calculated position of the at least one anatomical feature after the first portion of the orthopedic medical procedure.

2. The method of claim 1, further comprising providing on a display an output that corresponds to the differential measurement.

3. The method of claim 1, wherein a first one of the plurality of telemetry devices is a first electromagnetic receiver, wherein a second one of the plurality of telemetry devices is a second electromagnetic receiver, and wherein a third one of the plurality of telemetry devices is a magnetic field generator.

4. The method of claim 1, wherein the plurality of telemetry devices consists of a first telemetry device and a second telemetry device, wherein the first telemetry device is an electromagnetic receiver, and wherein the second telemetry device is a magnetic field generator.

5. The method of claim 1, wherein the plurality of telemetry devices are a plurality of radio frequency telemetry devices.

6. The method of claim 1, wherein the orthopedic medical procedure is a hip joint replacement procedure, and wherein the differential measurement is a leg length difference.

7. The method of claim 1, wherein the orthopedic medical procedure is a hip joint replacement procedure, and wherein the differential measurement is an offset.

8. The method of claim 1, wherein the step of tracking movement of the plurality of telemetry devices prior to the first portion of the orthopedic medical procedure comprises:
receiving and recording a first set of multiple relative positions and orientations of the plurality of telemetry devices.

9. The method of claim 8, wherein the step of calculating the position of the at least one anatomical feature prior to the first portion of the orthopedic medical procedure comprises:
best fitting the first set of multiple relative positions and orientations of the plurality of telemetry devices to a mathematical equation representing a kinematic model of the at least one anatomical feature.

10. The method of claim 9, wherein the orthopedic medical procedure is a hip joint replacement procedure.

11. The method of claim 10, wherein the at least one anatomical feature is the center of rotation of the hip joint.

12. The method of claim 11, wherein the mathematical equation is for a sphere.

13. The method of claim 9, wherein the first portion of the orthopedic medical procedure is the replacement of the patient's hip joint with a prosthetic joint.

14. The method of claim 8, wherein the step of tracking movement of the plurality of telemetry devices after the first portion of the orthopedic medical procedure comprises:
receiving and recording a second set of multiple relative positions and orientations of the plurality of telemetry devices.

15. The method of claim 14, wherein the step of calculating the position of the at least one anatomical feature after the first portion of the orthopedic medical procedure comprises:
best fitting the second set of multiple relative positions and orientations of the plurality of telemetry devices to a mathematical equation representing a kinematic model of the at least one anatomical feature.

16. The method of claim 15, wherein the orthopedic medical procedure is a hip joint replacement procedure, and wherein the first portion of the orthopedic medical procedure is the replacement of the patient's hip joint with a prosthetic joint.

17. The method of claim 1, wherein the orthopedic medical procedure is a hip joint replacement procedure, and wherein the differential measurement is cup prosthesis angle.

18. The method of claim 1, wherein the orthopedic medical procedure is a hip joint replacement procedure, and wherein the differential measurement is range of motion.

19. The method of claim 1, wherein the step of determining the differential measurement does not require holding the patient's body in any particular orientation.

20. The method of claim 1, further comprising:
comparing the differential measurement with an ideal measurement.

21. The method of claim 20, wherein the orthopedic medical procedure is a hip joint replacement procedure, and wherein the first portion of the orthopedic medical procedure is the replacement of the patient's hip joint with a first prosthetic joint, the method further comprising:
selecting a second prosthetic joint;
after a second portion of the orthopedic medical procedure, while moving the patient's body through a third range of motion, tracking movement of the plurality of telemetry devices relative to each other, and calculating the position of the at least one anatomical feature relative to the plurality of telemetry devices based on the movement of the plurality of telemetry devices; and
determining a new differential measurement in connection with the second portion of the orthopedic medical procedure, wherein the new differential measurement is based at least in part on the calculated position of the at least one anatomical feature before the first portion of the orthopedic medical procedure and on the calculated position of the at least one anatomical feature after the second portion of the orthopedic medical procedure, wherein the second portion of the orthopedic medical procedure is the replacement of the first prosthetic joint with the second prosthetic joint, and wherein the step of selecting the second prosthetic joint includes adjusting the first prosthetic joint such that the new differential measurement matches the ideal differential measurement.

22. The method of claim 1, wherein the method does not include using a medical image.

23. The method of claim 22, wherein the medical image consists of one image from the group consisting of the following: computed tomography scan, magnetic resonance image, ultrasound image, x-ray image, and fluoroscopic image.

24. The method of claim 1, wherein the method does not include physically registering the positions and orientations of the plurality of telemetry devices with respect to a medical image.

25. The method of claim 1, wherein the method does not include physically registering the positions and orientations of the plurality of telemetry devices with respect to the at least one anatomical feature.

26. The method of claim 1, wherein the first range of motion is different than the second range of motion.

27. An apparatus for making orthopedic measurements during an orthopedic medical procedure, the apparatus comprising:
a plurality of telemetry devices attached to a patient's body; and
a processing device coupled to each telemetry device of the plurality of telemetry devices via a respective communication link, the processing device comprising:
a storage device; and
a processor connected to the storage device, the storage device storing a processing device program for controlling the processor, wherein the processor is operative with the processing device program to:
track movement of the plurality of telemetry devices relative to each other when the patient's body is moved through a first range of motion prior to a first portion of the orthopedic medical procedure;
calculate the position of at least one anatomical feature of the patient's body relative to the plurality of telemetry devices based upon the movement of the plurality of telemetry devices prior to the first portion of the orthopedic medical procedure;
track movement of the plurality of telemetry devices relative to each other when the patient's body is moved through a second range of motion after the first portion of the orthopedic medical procedure;
calculate the position of the at least one anatomical feature of the patient's body relative to the plurality of telemetry devices based upon the movement of the plurality of telemetry devices after the first portion of the orthopedic medical procedure; and
determine a differential measurement in connection with the first portion of the orthopedic medical procedure, wherein the differential measurement is based at least in part on the calculated position of the at least one anatomical feature before the first portion of the orthopedic medical procedure and on the calculated position of the at least one anatomical feature after the first portion of the orthopedic medical procedure.

28. The apparatus of claim 27, wherein the processor is further operative with the processing device program to provide on a display an output that corresponds to the differential measurement.

29. The apparatus of claim 27, wherein a first one of the plurality of telemetry devices is a first electromagnetic receiver, wherein a second one of the plurality of telemetry devices is a second electromagnetic receiver, and wherein a third one of the plurality of telemetry devices is a magnetic field generator.

30. The apparatus of claim 27, wherein the plurality of telemetry devices consists of a first telemetry device and a second telemetry device, wherein the first telemetry device is an electromagnetic receiver, and wherein the second telemetry device is a magnetic field generator.

31. The apparatus of claim 27, wherein the plurality of telemetry devices are a plurality of radio frequency telemetry devices, and wherein the communication link between each radio frequency telemetry device of the plurality of radio frequency telemetry devices and the processing device is a wireless communication link.

32. The apparatus of claim 27, wherein the orthopedic medical procedure is a hip joint replacement procedure, and wherein the differential measurement is a leg length difference.

33. The apparatus of claim 27, wherein the orthopedic medical procedure is a hip joint replacement procedure, and wherein the differential measurement is an offset.

34. The apparatus of claim 27, wherein the processor is operative with the processing device program to track the movement of the plurality of telemetry devices relative to each other prior to the first portion of the orthopedic medical procedure by receiving and recording a first set of multiple relative positions and orientations of the plurality of telemetry devices.

35. The apparatus of claim 34, wherein the processor is operative with the processing device program to calculate the position of the at least one anatomical feature prior to the first portion of the orthopedic medical procedure by best fitting the first set of multiple relative positions and orientations of the plurality of telemetry devices to a mathematical equation representing a kinematic model of the at least one anatomical feature.

36. The apparatus of claim 35, wherein the orthopedic medical procedure is a hip joint replacement procedure.

37. The apparatus of claim 36, wherein the at least one anatomical feature is the center of rotation of the hip joint.

38. The apparatus of claim 37, wherein the mathematical equation is for a sphere.

39. The apparatus of claim 35, wherein the first portion of the orthopedic medical procedure is the replacement of the patient's hip joint with a prosthetic joint.

40. The apparatus of claim 34, wherein the processor is operative with the processing device program to track the movement of the plurality of telemetry devices relative to each other after the first portion of the orthopedic medical procedure by receiving and recording a second set of multiple relative positions and orientations of the plurality of telemetry devices.

41. The apparatus of claim 40, wherein the processor is operative with the processing device program to calculate the position of the at least one anatomical feature after the first portion of the orthopedic medical procedure by best fitting the second set of multiple relative positions and orientations of the plurality of telemetry devices to a mathematical equation representing a kinematic model of the at least one anatomical feature.

42. The apparatus of claim 41, wherein the orthopedic medical procedure is a hip joint replacement procedure, and wherein the first portion of the orthopedic medical procedure is the replacement of the patient's hip joint with a prosthetic joint.

43. The apparatus of claim 27, wherein the orthopedic medical procedure is a hip joint replacement procedure, and wherein the differential measurement is cup prosthesis angle.

44. The apparatus of claim 27, wherein the orthopedic medical procedure is a hip joint replacement procedure, and wherein the differential measurement is range of motion.

45. The apparatus of claim 27, wherein the processor is operative with the processing device program to determine the differential measurement without the patient's body being held in any particular orientation.

46. The apparatus of claim 27, wherein the processor is further operative with the processing device program to compare the differential measurement with an ideal measurement.

47. The apparatus of claim 46, wherein the orthopedic medical procedure is a hip joint replacement procedure, wherein the first portion of the orthopedic medical procedure is the replacement of the patient's hip joint with a first prosthetic joint, and wherein the processor is further operative with the processing device program to:
select a second prosthetic joint;
track movement of the plurality of telemetry devices relative to each other when the patient's body is moved through a third range of motion after a second portion of the orthopedic medical procedure;
calculate the position of the at least one anatomical feature of the patient's body relative to the plurality of telemetry devices based upon the movement of the plurality of telemetry devices after the second portion of the orthopedic medical procedure; and
determine a new differential measurement in connection with the second portion of the orthopedic medical procedure, wherein the new differential measurement is based at least in part on the calculated position of the at least one anatomical feature before the first portion of the orthopedic medical procedure and on the calculated position of the at least one anatomical feature after the second portion of the orthopedic medical procedure, wherein the second portion of the orthopedic medical procedure is the replacement of the first prosthetic joint with the second prosthetic joint, and wherein the processor is operative with the processing device program to select the second prosthetic joint by adjusting the first prosthetic joint such that the new differential measurement matches the ideal differential measurement.

48. The apparatus of claim 27, wherein the processor is operative with the processing device program to calculate the position of the at least one anatomical feature without using a medical image.

49. The apparatus of claim 48, wherein the medical image consists of one image from the group consisting of the following: computed tomography scan, magnetic resonance image, ultrasound image, x-ray image, and fluoroscopic image.

50. The apparatus of claim 27, wherein the processor is operative with the processing device program to calculate the position of the at least one anatomical feature without physically registering the positions and orientations of the plurality of telemetry devices with respect to a medical image.

51. The apparatus of claim 27, wherein the processor is operative with the processing device program to calculate the position of the at least one anatomical feature without physically registering the positions and orientations of the plurality of telemetry devices with respect to the at least one anatomical feature.

52. The apparatus of claim 27, wherein the first range of motion is different than the second range of motion.

53. The apparatus of claim 27, wherein the processor is further operative with the processing device program to:
calculate the orientation of the at least one anatomical feature of the patient's body at which an orthopedic measurement is most accurate; and
provide on a display an output that indicates when the at least one anatomical feature is in that calculated orientation.

54. An apparatus for attachment of a telemetry device to a bone of a patient in an orthopedic medical procedure, the apparatus comprising:
a U-shaped piece having a front face and a back face;
a bone screw; and
an anti-rotation pin, wherein the U-shaped piece has a hole extending therethrough from the front face to the back face for receiving the bone screw, and wherein the anti-rotation pin extends from the back face of the U-shaped piece.

55. The apparatus of claim 54, wherein an end portion of the anti-rotation pin that is inserted into the bone has three substantially triangular faces to prevent rotation of the U-shaped piece.

56. The apparatus of claim 54, wherein the U-shaped piece has a rectangular opening extending from the front face to the back face.

57. The apparatus of claim 56, wherein the rectangular opening in the U-shaped piece receives the telemetry device.

58. The apparatus of claim 54, wherein the telemetry device is encased within a telemetry device housing, and wherein the U-shaped piece is integral with the telemetry device housing.

59. The apparatus of claim 58, wherein U-shaped piece and the telemetry device housing are a one-piece plastic injection molding.

60. The apparatus of claim 54, wherein the telemetry device is an electromagnetic receiver, and wherein the U-shaped piece, the bone screw, and the anti-rotation pin are each constructed of a non-magnetic material.

61. An apparatus for attachment of a telemetry device to a bone of a patient in an orthopedic medical procedure, the apparatus comprising:
a U-shaped channel for receiving the telemetry device having two side portions and a base portion; and
a plurality of pins, wherein the base portion of the U-shaped channel has a plurality of holes to receive the plurality of pins, and wherein each pin of the plurality of pins has a sharpened end portion for insertion into the bone.

62. The apparatus of claim 61, further comprising a driver, wherein the driver is received within the confines of the U-shaped channel to drive the pins into the bone.

63. The apparatus of claim 61, wherein the two side portions of the U-shaped channel exert a force on the telemetry device to hold the telemetry device in place within the U-shaped channel.

64. The apparatus of claim 61, wherein the telemetry device is an electromagnetic receiver, and wherein the U-shaped channel and the pins are each constructed of a non-magnetic material.

* * * * *